(12) United States Patent
Soto et al.

(10) Patent No.: US 11,096,754 B2
(45) Date of Patent: Aug. 24, 2021

(54) STERILE DRAPE ASSEMBLY FOR SURGICAL ROBOT

(71) Applicant: MAKO Surgical Corp., Ft. Lauderdale, FL (US)

(72) Inventors: Victor Soto, Doral, FL (US); Oscar Williams, Ft. Lauderdale, FL (US); Donald W. Malackowski, Schoolcraft, MI (US); Kathryn Aubrey, Miami, FL (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 223 days.

(21) Appl. No.: 16/151,439

(22) Filed: Oct. 4, 2018

(65) Prior Publication Data

US 2019/0099232 A1    Apr. 4, 2019

Related U.S. Application Data

(60) Provisional application No. 62/567,993, filed on Oct. 4, 2017.

(51) Int. Cl.
*A61B 46/10* (2016.01)
*A61B 34/30* (2016.01)
(Continued)

(52) U.S. Cl.
CPC .............. *A61B 46/10* (2016.02); *A61B 34/30* (2016.02); *A61B 46/23* (2016.02); *A61B 90/39* (2016.02);
(Continued)

(58) Field of Classification Search
CPC ......... A61B 46/10; A61B 90/39; A61B 46/23; A61B 34/30; A61B 46/40;
(Continued)

(56) References Cited

U.S. PATENT DOCUMENTS 3,482,567 A    12/1969  Franklin
3,483,494 A    12/1969  Cromie
(Continued)

FOREIGN PATENT DOCUMENTS

AU    754882 B2    11/2002
GB    2483154 A    2/2012
(Continued)

OTHER PUBLICATIONS

Bateman, D.A., "Adjustable Mirror Mount Design Using Kinematic Principles" Dip. Tech.—Royal Aircraft Establishment—Technical Report No. 66349, Nov. 1966. U.D.C. No. 621.3-21: 531.1: 681.4. 28 pages.
(Continued)

*Primary Examiner* — Catherine M Voorhees
(74) *Attorney, Agent, or Firm* — Howard & Howard Attorneys PLLC

(57) ABSTRACT

A sterile drape assembly for a surgical robot having a robotic arm, a cart coupled to the robotic arm, and optical tracking elements coupled to the robotic arm. The sterile drape assembly includes a surgical drape having an arm drape portion adapted to be disposed over the robotic arm. The sterile drape assembly also includes a drape holder cooperating with the surgical drape to cover the optical tracking elements located on the robotic arm.

13 Claims, 15 Drawing Sheets

(51) Int. Cl.
  *A61B 34/20* (2016.01)
  *A61B 90/00* (2016.01)
  *A61B 46/23* (2016.01)
(52) U.S. Cl.
  CPC ............... *A61B 2034/2055* (2016.02); *A61B 2034/2072* (2016.02); *A61B 2090/3983* (2016.02)
(58) Field of Classification Search
  CPC .... A61B 2090/3983; A61B 2034/2072; A61B 2034/2055
  See application file for complete search history.

(56) References Cited

U.S. PATENT DOCUMENTS

| | | | |
|---|---|---|---|
| 3,796,477 | A | 3/1974 | Geraci |
| 4,409,738 | A | 10/1983 | Renander et al. |
| 4,522,196 | A | 6/1985 | Cunningham et al. |
| 4,770,497 | A | 9/1988 | Brown |
| 5,042,981 | A | 8/1991 | Gross |
| 5,080,108 | A | 1/1992 | Roth |
| 5,122,904 | A * | 6/1992 | Fujiwara ............ A61B 90/25 359/510 |
| 5,184,601 | A | 2/1993 | Putman |
| 5,274,500 | A | 12/1993 | Dunn |
| 5,413,573 | A | 5/1995 | Koivukangas |
| 5,433,221 | A | 7/1995 | Adair |
| 5,441,042 | A | 8/1995 | Putman |
| 5,457,962 | A | 10/1995 | Faries, Jr. et al. |
| 5,467,223 | A * | 11/1995 | Cleveland, Jr. ........ A61B 46/10 359/510 |
| 5,524,643 | A | 6/1996 | Faries, Jr. et al. |
| 5,574,561 | A | 11/1996 | Boudreau et al. |
| 5,591,119 | A | 1/1997 | Adair |
| 5,626,216 | A | 5/1997 | Sperling et al. |
| 5,642,956 | A | 7/1997 | Hale |
| 5,653,938 | A * | 8/1997 | Faries, Jr. ............ A61L 2/28 422/105 |
| 5,669,152 | A | 9/1997 | McMurtry |
| 5,762,458 | A | 6/1998 | Wang et al. |
| 5,769,554 | A | 6/1998 | Slocum |
| 5,785,643 | A | 7/1998 | Lynn |
| 5,800,483 | A | 9/1998 | Vought |
| 5,816,252 | A | 10/1998 | Faries, Jr. et al. |
| 5,853,363 | A | 12/1998 | Vought |
| 5,855,583 | A | 1/1999 | Wang et al. |
| 5,857,467 | A | 1/1999 | Faries, Jr. et al. |
| 5,876,328 | A | 3/1999 | Fox et al. |
| 5,891,020 | A | 4/1999 | Luber et al. |
| 5,960,794 | A | 10/1999 | Shaw |
| 6,050,981 | A | 4/2000 | Lampropoulos et al. |
| 6,063,095 | A | 5/2000 | Wang et al. |
| 6,065,898 | A | 5/2000 | Hale |
| 6,072,569 | A | 6/2000 | Bowen |
| 6,091,058 | A * | 7/2000 | Fanes, Jr. ............ A61F 7/0085 219/430 |
| 6,102,044 | A | 8/2000 | Naidyhorski |
| 6,102,850 | A | 8/2000 | Wang et al. |
| 6,105,578 | A | 8/2000 | Sommers et al. |
| 6,123,080 | A | 9/2000 | Mohan et al. |
| 6,132,368 | A | 10/2000 | Cooper |
| 6,228,089 | B1 | 5/2001 | Wahrburg |
| 6,325,351 | B1 | 12/2001 | Hale et al. |
| 6,330,837 | B1 | 12/2001 | Charles et al. |
| 6,331,181 | B1 | 12/2001 | Tierney et al. |
| 6,346,072 | B1 | 2/2002 | Cooper |
| 6,357,445 | B1 | 3/2002 | Shaw |
| 6,371,121 | B1 | 4/2002 | Faries, Jr. et al. |
| 6,375,610 | B2 | 4/2002 | Verschuur |
| 6,416,462 | B1 | 7/2002 | Tovey et al. |
| 6,431,530 | B1 | 8/2002 | Stamps et al. |
| 6,436,107 | B1 | 8/2002 | Wang et al. |
| 6,460,436 | B1 | 10/2002 | Salzer et al. |
| 6,471,172 | B1 | 10/2002 | Lemke et al. |
| 6,491,701 | B2 | 12/2002 | Tierney et al. |
| 6,612,310 | B2 | 9/2003 | Sklar |
| 6,661,955 | B1 | 12/2003 | Calvet et al. |
| 6,679,267 | B2 | 1/2004 | McNeirney et al. |
| 6,692,141 | B2 | 2/2004 | Jesurun et al. |
| 6,697,664 | B2 | 2/2004 | Kienzle, III et al. |
| 6,699,177 | B1 | 3/2004 | Wang et al. |
| 6,720,988 | B1 | 4/2004 | Gere et al. |
| 6,755,195 | B1 | 6/2004 | Lemke et al. |
| 6,804,547 | B2 | 10/2004 | Pelzer et al. |
| 6,805,453 | B2 | 10/2004 | Spetzler et al. |
| 6,810,881 | B2 | 11/2004 | Faries, Jr. et al. |
| 6,843,252 | B2 | 1/2005 | Harrison et al. |
| 6,860,271 | B2 | 3/2005 | Faries, Jr. et al. |
| 6,863,071 | B2 | 3/2005 | Annett et al. |
| 6,866,671 | B2 | 3/2005 | Tierney et al. |
| 6,910,485 | B2 | 6/2005 | Faries, Jr. et al. |
| 6,918,395 | B2 | 7/2005 | Faries, Jr. et al. |
| 7,002,102 | B2 | 2/2006 | Münch et al. |
| 7,044,132 | B2 | 5/2006 | Masini |
| 7,048,745 | B2 | 5/2006 | Tierney et al. |
| 7,074,180 | B2 | 7/2006 | Bertolero et al. |
| 7,118,582 | B1 | 10/2006 | Wang et al. |
| 7,122,032 | B2 | 10/2006 | Shinmura et al. |
| 7,331,967 | B2 | 2/2008 | Lee et al. |
| 7,347,210 | B2 | 3/2008 | Faries, Jr. et al. |
| 7,350,373 | B1 | 4/2008 | Faries, Jr. et al. |
| 7,357,774 | B2 | 4/2008 | Cooper |
| 7,418,966 | B2 | 9/2008 | Faries, Jr. et al. |
| 7,524,320 | B2 | 4/2009 | Tierney et al. |
| 7,666,191 | B2 | 2/2010 | Orban, III et al. |
| 7,699,855 | B2 | 4/2010 | Anderson et al. |
| 7,727,244 | B2 | 6/2010 | Orban, III et al. |
| 7,775,213 | B2 | 8/2010 | Henke-Sarmento et al. |
| 7,789,874 | B2 | 9/2010 | Yu et al. |
| 7,819,885 | B2 | 10/2010 | Cooper |
| 7,820,446 | B2 | 10/2010 | Feilkas et al. |
| 7,850,602 | B2 | 12/2010 | Humble et al. |
| 7,850,642 | B2 | 12/2010 | Moll et al. |
| 7,886,743 | B2 | 2/2011 | Cooper et al. |
| 7,947,050 | B2 | 5/2011 | Lee et al. |
| 7,947,051 | B2 | 5/2011 | Lee et al. |
| 7,955,322 | B2 | 6/2011 | Devengenzo et al. |
| 7,959,860 | B2 | 6/2011 | Faries, Jr. et al. |
| 7,963,288 | B2 | 6/2011 | Rosenberg et al. |
| 7,963,913 | B2 | 6/2011 | Devengenzo et al. |
| 7,972,298 | B2 | 7/2011 | Wallace et al. |
| 7,974,681 | B2 | 7/2011 | Wallace et al. |
| 8,005,537 | B2 | 8/2011 | Hlavka et al. |
| 8,021,326 | B2 | 9/2011 | Moll et al. |
| 8,052,636 | B2 | 11/2011 | Moll et al. |
| 8,054,184 | B2 | 11/2011 | Cline et al. |
| 8,074,657 | B2 | 12/2011 | Scott et al. |
| 8,105,319 | B2 | 1/2012 | Doyle et al. |
| 8,105,338 | B2 | 1/2012 | Anderson et al. |
| 8,142,447 | B2 | 3/2012 | Cooper et al. |
| 8,146,825 | B1 | 4/2012 | Prpa |
| 8,148,666 | B2 | 4/2012 | Faries, Jr. et al. |
| 8,182,469 | B2 | 5/2012 | Anderson et al. |
| 8,182,470 | B2 | 5/2012 | Devengenzo et al. |
| 8,190,238 | B2 | 5/2012 | Moll et al. |
| 8,196,586 | B2 | 6/2012 | Henke-Sarmento et al. |
| 8,202,278 | B2 | 6/2012 | Orban, III et al. |
| 8,206,053 | B2 | 6/2012 | Bennett et al. |
| 8,206,406 | B2 | 6/2012 | Orban, III |
| 8,216,250 | B2 | 7/2012 | Orban, III et al. |
| 8,220,468 | B2 | 7/2012 | Cooper et al. |
| 8,225,495 | B2 | 7/2012 | Dehler |
| 8,241,208 | B2 | 8/2012 | Jiang et al. |
| 8,257,303 | B2 | 9/2012 | Moll et al. |
| 8,264,767 | B2 | 9/2012 | Nozawa |
| 8,273,076 | B2 | 9/2012 | Devengenzo et al. |
| 8,286,637 | B2 | 10/2012 | Kaska |
| 8,311,626 | B2 | 11/2012 | Hlavka et al. |
| 8,375,808 | B2 | 2/2013 | Blumenkranz et al. |
| 8,394,054 | B2 | 3/2013 | Wallace et al. |
| 8,409,136 | B2 | 4/2013 | Wallace et al. |
| 8,413,948 | B2 | 4/2013 | Kemeny |
| 8,460,277 | B2 | 6/2013 | Suarez et al. |

(56) References Cited

U.S. PATENT DOCUMENTS

| | | |
|---|---|---|
| 8,464,722 B2 | 6/2013 | Chua |
| 8,469,947 B2 | 6/2013 | Devengenzo et al. |
| 8,529,582 B2 | 9/2013 | Devengenzo et al. |
| 8,534,848 B2 | 9/2013 | Hauri et al. |
| 8,548,779 B2 | 10/2013 | Ortmaier et al. |
| 8,602,031 B2 | 12/2013 | Reis et al. |
| 8,608,773 B2 | 12/2013 | Tierney et al. |
| 8,640,706 B2 | 2/2014 | Skora et al. |
| 8,662,082 B2 | 3/2014 | Bogojevic et al. |
| 8,672,922 B2 | 3/2014 | Loh et al. |
| 8,678,009 B2 | 3/2014 | Hagn |
| 8,720,448 B2 | 5/2014 | Reis et al. |
| 8,740,881 B2 | 6/2014 | Ortmaier et al. |
| 8,746,252 B2 | 6/2014 | McGrogan et al. |
| 8,776,800 B2 | 7/2014 | Skora et al. |
| 8,784,435 B2 | 7/2014 | Cooper et al. |
| 8,844,538 B2 | 9/2014 | Stang |
| 8,888,764 B2 | 11/2014 | Devengenzo et al. |
| 8,894,634 B2 | 11/2014 | Devengenzo et al. |
| 8,910,637 B2 | 12/2014 | Winer |
| 8,945,095 B2 | 2/2015 | Blumenkranz et al. |
| 8,998,799 B2 | 4/2015 | Orban, III et al. |
| 8,998,930 B2 | 4/2015 | Orban, III |
| 9,033,958 B2 | 5/2015 | Mailloux et al. |
| 9,044,269 B2 * | 6/2015 | Woerlein ............... A61B 90/39 |
| 9,096,033 B2 | 8/2015 | Holop et al. |
| 9,161,816 B2 | 10/2015 | Ball et al. |
| 9,168,103 B2 | 10/2015 | Hladio et al. |
| 9,259,277 B2 | 2/2016 | Rogers et al. |
| 9,265,582 B2 | 2/2016 | Riviere et al. |
| 9,283,041 B2 | 3/2016 | Adams |
| 9,295,521 B2 | 3/2016 | Pack et al. |
| 9,307,945 B2 | 4/2016 | Campista |
| 9,320,568 B2 | 4/2016 | Orban, III et al. |
| 9,629,680 B2 | 4/2017 | Winer |
| 9,713,498 B2 | 7/2017 | Malackowski et al. |
| 9,724,163 B2 | 8/2017 | Orban |
| 9,737,373 B2 | 8/2017 | Schuh |
| 9,883,915 B2 | 2/2018 | Rogers et al. |
| 9,993,310 B2 | 6/2018 | Pecora |
| 10,039,610 B2 | 8/2018 | Allen |
| 10,052,761 B2 | 8/2018 | Langenfeld |
| 10,085,803 B2 | 10/2018 | Higuchi et al. |
| 10,149,731 B2 | 12/2018 | Adams |
| 10,188,475 B2 | 1/2019 | Chua et al. |
| 10,213,267 B2 | 2/2019 | King et al. |
| 10,226,219 B2 | 3/2019 | Cheatham, III et al. |
| 10,235,737 B2 | 3/2019 | Cheatham, III et al. |
| 10,278,659 B2 | 5/2019 | Kim |
| 10,285,767 B2 | 5/2019 | Marinchak |
| 10,293,497 B2 | 5/2019 | Lohmeier et al. |
| 10,335,242 B2 | 7/2019 | Devengenzo et al. |
| 10,342,625 B2 | 7/2019 | Loh et al. |
| 10,357,324 B2 | 7/2019 | Flatt et al. |
| 10,398,522 B2 | 9/2019 | Czajka, Jr. et al. |
| 10,433,925 B2 | 10/2019 | Shelton, IV et al. |
| 10,485,619 B2 | 11/2019 | Rogers et al. |
| 10,485,621 B2 | 11/2019 | Morrissette et al. |
| 10,537,358 B2 | 1/2020 | McGrogan et al. |
| 10,603,126 B2 | 3/2020 | Karguth et al. |
| 10,610,312 B2 | 4/2020 | Srivastava et al. |
| 10,639,110 B2 | 5/2020 | Hares |
| 2002/0137358 A1 | 9/2002 | Binnard et al. |
| 2004/0077939 A1 * | 4/2004 | Graumann ............ A61B 34/30 600/424 |
| 2005/0088763 A1 | 4/2005 | Weaver et al. |
| 2006/0100610 A1 | 5/2006 | Wallace et al. |
| 2006/0161138 A1 | 7/2006 | Orban, III et al. |
| 2006/0191540 A1 | 8/2006 | Lamprich et al. |
| 2007/0267028 A1 | 11/2007 | Junk |
| 2007/0282311 A1 | 12/2007 | Scott et al. |
| 2008/0147089 A1 | 6/2008 | Loh et al. |
| 2008/0218770 A1 | 9/2008 | Moll et al. |
| 2008/0236598 A1 | 10/2008 | Gobel |
| 2009/0088772 A1 | 4/2009 | Blumenkranz |
| 2009/0248039 A1 | 10/2009 | Cooper et al. |
| 2010/0065068 A1 | 3/2010 | Hamazaki et al. |
| 2010/0170519 A1 | 7/2010 | Romo et al. |
| 2010/0241137 A1 | 9/2010 | Doyle et al. |
| 2010/0268249 A1 | 10/2010 | Stuart |
| 2010/0268250 A1 | 10/2010 | Stuart et al. |
| 2010/0308195 A1 | 12/2010 | Yu et al. |
| 2011/0087238 A1 | 4/2011 | Wang et al. |
| 2011/0088702 A1 | 4/2011 | King et al. |
| 2011/0190790 A1 | 8/2011 | Summerer et al. |
| 2011/0213383 A1 | 9/2011 | Lee et al. |
| 2011/0238083 A1 | 9/2011 | Moll et al. |
| 2011/0277775 A1 | 11/2011 | Holop et al. |
| 2011/0277776 A1 | 11/2011 | McGrogan et al. |
| 2012/0065472 A1 | 3/2012 | Doyle et al. |
| 2012/0071752 A1 | 3/2012 | Sewell et al. |
| 2012/0071821 A1 | 3/2012 | Yu |
| 2012/0071822 A1 | 3/2012 | Romo et al. |
| 2012/0071894 A1 | 3/2012 | Tanner et al. |
| 2012/0071895 A1 | 3/2012 | Stahler et al. |
| 2012/0080040 A1 | 4/2012 | Skora et al. |
| 2012/0080041 A1 | 4/2012 | Skora et al. |
| 2012/0083799 A1 | 4/2012 | Chen et al. |
| 2012/0083825 A1 | 4/2012 | Stroup et al. |
| 2012/0191107 A1 | 7/2012 | Tanner et al. |
| 2012/0209174 A1 | 8/2012 | Moll et al. |
| 2012/0209291 A1 | 8/2012 | Anderson et al. |
| 2012/0232566 A1 | 9/2012 | Orban, III et al. |
| 2012/0239060 A1 | 9/2012 | Orban, III |
| 2012/0247489 A1 | 10/2012 | Orban, III et al. |
| 2012/0289974 A1 | 11/2012 | Rogers et al. |
| 2012/0305650 A1 * | 12/2012 | Prpa ............... A61B 90/96 235/470 |
| 2012/0312308 A1 | 12/2012 | Allen |
| 2013/0035537 A1 | 2/2013 | Wallace et al. |
| 2013/0092177 A1 | 4/2013 | Chua et al. |
| 2013/0174858 A1 | 7/2013 | Annett |
| 2013/0211401 A1 | 8/2013 | Bailey et al. |
| 2013/0231679 A1 | 9/2013 | Wallace et al. |
| 2013/0247921 A1 | 9/2013 | Dye et al. |
| 2013/0331858 A1 | 12/2013 | Devengenzo et al. |
| 2014/0039681 A1 | 2/2014 | Bowling et al. |
| 2014/0130810 A1 | 5/2014 | Azizian et al. |
| 2014/0171965 A1 | 6/2014 | Loh et al. |
| 2014/0261456 A1 * | 9/2014 | Malackowski ........ A61B 34/20 128/849 |
| 2014/0318551 A1 | 10/2014 | Daly |
| 2014/0326254 A1 | 11/2014 | McGrogan et al. |
| 2015/0047647 A1 | 2/2015 | Winer |
| 2015/0073437 A1 | 3/2015 | Devengenzo et al. |
| 2015/0133960 A1 | 5/2015 | Lohmeier et al. |
| 2015/0142012 A1 | 5/2015 | Lohmeier et al. |
| 2015/0148817 A1 | 5/2015 | Lohmeier et al. |
| 2015/0148818 A1 | 5/2015 | Lohmeier et al. |
| 2015/0150638 A1 | 6/2015 | Lohmeier et al. |
| 2015/0173841 A1 | 6/2015 | Orban |
| 2015/0202009 A1 | 7/2015 | Nussbaumer et al. |
| 2015/0305815 A1 | 10/2015 | Holop et al. |
| 2015/0342685 A1 | 12/2015 | Livesey |
| 2016/0008073 A1 | 1/2016 | Pecora |
| 2016/0058513 A1 | 3/2016 | Giorgi et al. |
| 2016/0242861 A1 | 8/2016 | Flatt et al. |
| 2016/0310224 A1 | 10/2016 | Dye et al. |
| 2016/0324583 A1 | 11/2016 | Kheradpir et al. |
| 2017/0000572 A1 | 1/2017 | Moctezuma de la Barrera et al. |
| 2017/0086934 A1 | 3/2017 | Devengenzo et al. |
| 2017/0290632 A1 | 10/2017 | Nakatsu et al. |
| 2017/0333136 A1 | 11/2017 | Hladio et al. |
| 2017/0333147 A1 | 11/2017 | Bernstein |
| 2017/0348063 A1 | 12/2017 | Braun et al. |
| 2018/0000472 A1 | 1/2018 | Beira |
| 2018/0036091 A1 | 2/2018 | Scholan |
| 2018/0055593 A1 | 3/2018 | Schlatterer |
| 2018/0116746 A1 * | 5/2018 | Lennertz ............... A61B 34/20 |
| 2018/0125597 A1 | 5/2018 | Gogarty et al. |
| 2018/0132959 A1 | 5/2018 | Marshall et al. |
| 2018/0140371 A1 | 5/2018 | Hares et al. |
| 2018/0200014 A1 | 7/2018 | Bonny et al. |
| 2018/0206931 A1 | 7/2018 | Scheib |

(56) References Cited

U.S. PATENT DOCUMENTS

| | | |
|---|---|---|
| 2018/0215051 A1 | 8/2018 | Kan |
| 2018/0289438 A1 | 10/2018 | Pennoyer |
| 2018/0296292 A1 | 10/2018 | Yamasaki et al. |
| 2018/0325616 A1 | 11/2018 | Kapadia et al. |
| 2019/0039241 A1 | 2/2019 | Langenfeld et al. |
| 2019/0046284 A1 | 2/2019 | Pennoyer et al. |
| 2019/0053866 A1 | 2/2019 | Seow et al. |
| 2019/0069969 A1 | 3/2019 | Higuchi et al. |
| 2019/0076204 A1 | 3/2019 | Robertson et al. |
| 2019/0099232 A1 | 4/2019 | Soto et al. |
| 2019/0142540 A1 | 5/2019 | Chow |
| 2019/0151040 A1 | 5/2019 | Chua et al. |
| 2019/0223965 A1 | 7/2019 | Marshall et al. |
| 2019/0223969 A1 | 7/2019 | Ramstad et al. |
| 2019/0239969 A1 | 8/2019 | Abu-Akeel et al. |
| 2019/0247134 A1 | 8/2019 | Marinchak |
| 2019/0282313 A1 | 9/2019 | Devengenzo et al. |
| 2019/0282315 A1 | 9/2019 | Loh et al. |
| 2019/0290378 A1 | 9/2019 | Schwagli et al. |
| 2019/0298469 A1 | 10/2019 | Ramstad et al. |
| 2019/0321120 A1 | 10/2019 | Hutchison et al. |
| 2020/0000490 A1 | 1/2020 | McGrogan et al. |
| 2020/0046207 A1 | 2/2020 | Calavrezos et al. |
| 2020/0046442 A1 | 2/2020 | Rogers et al. |
| 2020/0069383 A1 | 3/2020 | Betsugi et al. |
| 2020/0069386 A1 | 3/2020 | Betsugi et al. |
| 2020/0069389 A1 | 3/2020 | Morrissette et al. |
| 2020/0069390 A1 | 3/2020 | Betsugi et al. |
| 2020/0093556 A1 | 3/2020 | Zemlok et al. |
| 2020/0170724 A1 | 6/2020 | Flatt et al. |
| 2020/0170740 A1 | 6/2020 | Galili et al. |
| 2020/0179072 A1 | 6/2020 | Pennoyer et al. |
| 2020/0188050 A1 | 6/2020 | Pennoyer et al. |
| 2020/0205641 A1 | 7/2020 | Luck et al. |
| 2020/0205793 A1 | 7/2020 | Jang et al. |

FOREIGN PATENT DOCUMENTS

| | | |
|---|---|---|
| GB | 2570514 A | 7/2019 |
| GB | 2572333 A | 10/2019 |
| WO | 2009092701 A1 | 7/2009 |
| WO | 2009123891 A1 | 10/2009 |
| WO | 2009123925 A1 | 10/2009 |
| WO | 2010121107 A1 | 10/2010 |
| WO | 2010121117 A1 | 10/2010 |
| WO | 2013075204 A1 | 5/2013 |
| WO | 2013075205 A1 | 5/2013 |
| WO | 20130159932 A1 | 10/2013 |
| WO | 2014162217 A1 | 10/2014 |
| WO | 2014165828 A1 | 10/2014 |
| WO | 2015052629 A1 | 4/2015 |
| WO | 2015110542 A1 | 7/2015 |
| WO | 2017144115 A1 | 8/2017 |
| WO | 2018189729 A1 | 10/2018 |
| WO | 2019096933 A2 | 5/2019 |
| WO | 2019108567 A1 | 6/2019 |
| WO | 2019150086 A1 | 8/2019 |
| WO | 2019150111 A1 | 8/2019 |
| WO | 2019195841 A1 | 10/2019 |

OTHER PUBLICATIONS

Culpepper, Martin L. et al., "Design of Low-Cost Kinematic Couplings Using Formed Balls and Grooves in Sheet Metal Parts", (Massachusetts Institute of Technology, Cambridge, MA, Oct. 2003, 4 pages.

English language abstract for WO 2009/092701 extracted from espacenet.com database on Nov. 12, 2018, 2 pages.

English language abstract for WO 2013/159932 extracted from espacenet.com database on Nov. 12, 2018, 2 pages.

Furse, J.E., Instrument Science and Technology "Kinematic design of fine mechanisms in instruments", Engineering Services, National Physical Laboratory, Teddington, Middlesex, UK, J. Phys. E: Sol. Instrum., vol. 14, 1981, 8 pages.

Hale, Layton C. et al., "Optimal Design Techniques for Kinematic Couplings", Precision Engineering Journal of the International Societies for Precision Engineering and Nanotechnology 25 (2001) 114-127, 14 pages.

International Search Report for International Application No. PCT/US2016/018691 dated Jun. 1, 2016, 3 pages.

Slocum, Alexander, "Design of three-grove kinematic couplings", Department of Mechanical Engineering, Massachusetts Institute of Technology, Cambridge, MA, USA, 1992, Butterworth-Heinemann, 10 pages.

* cited by examiner

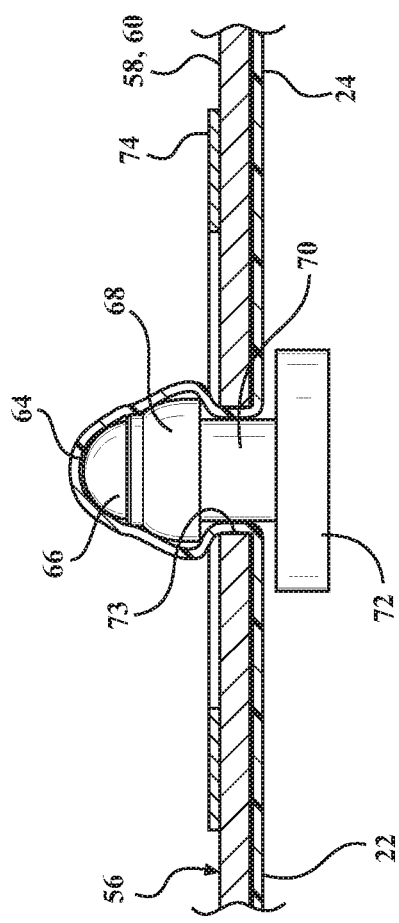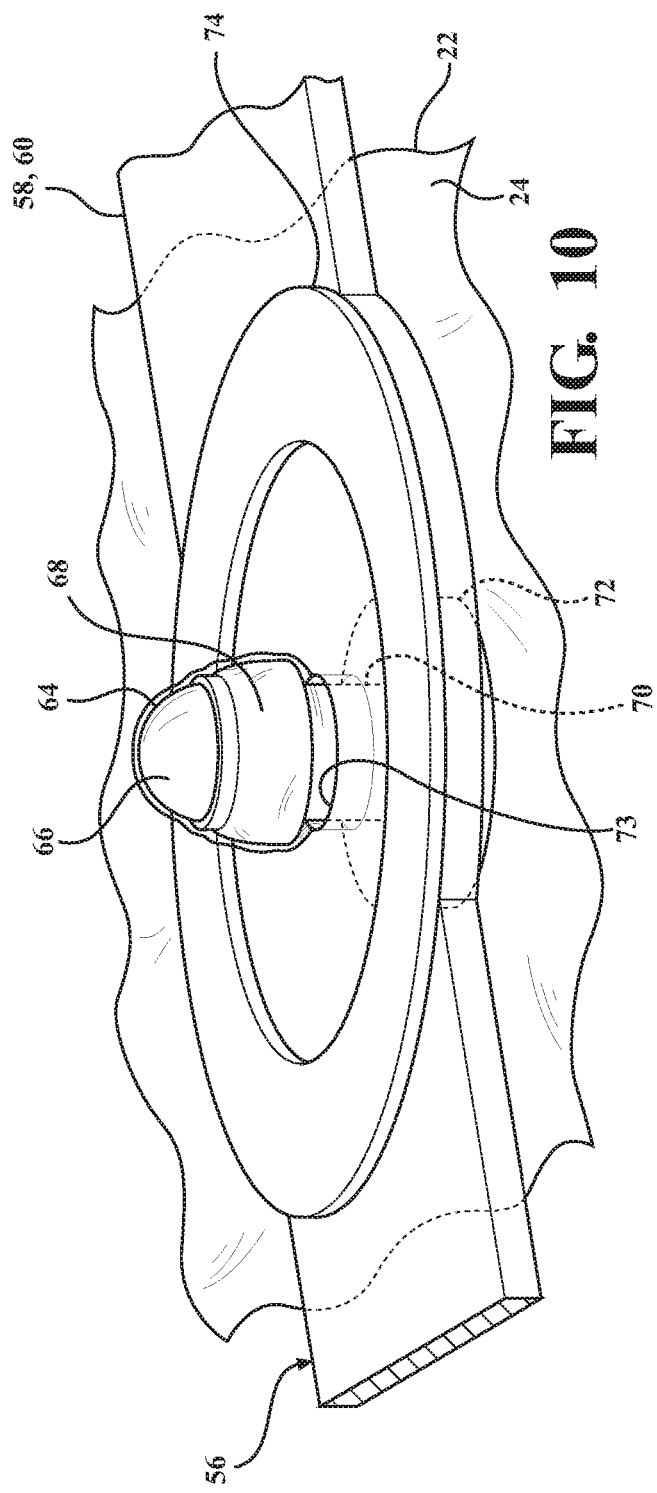

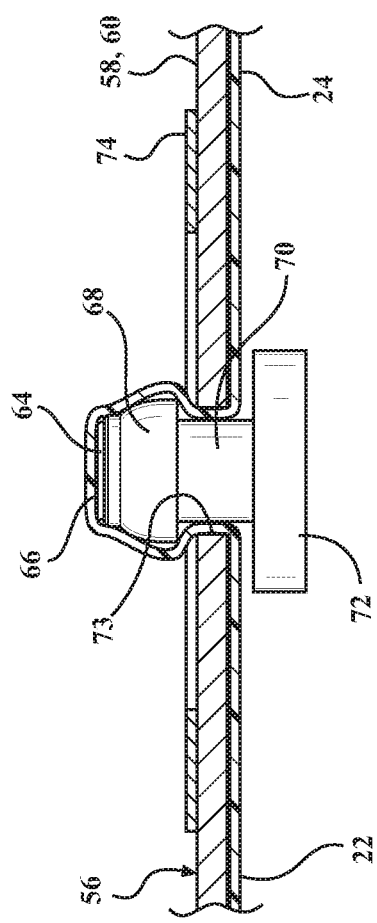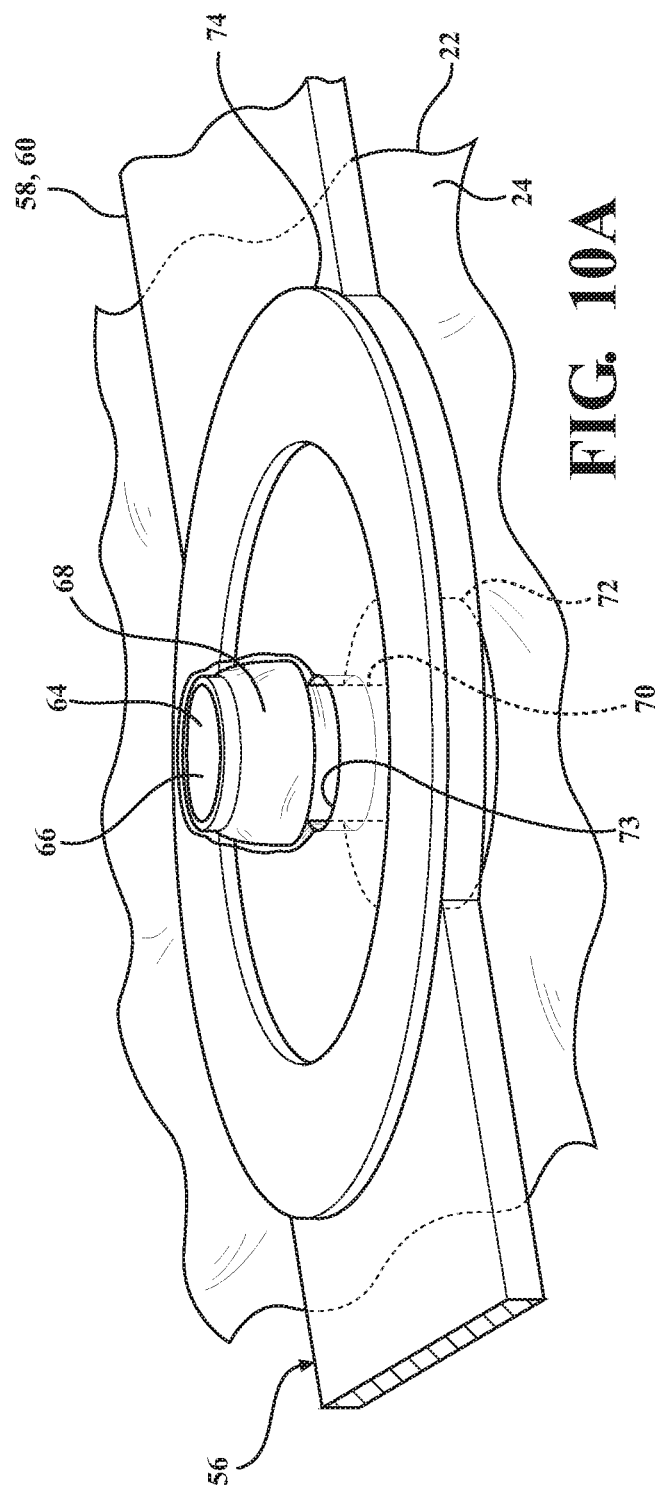

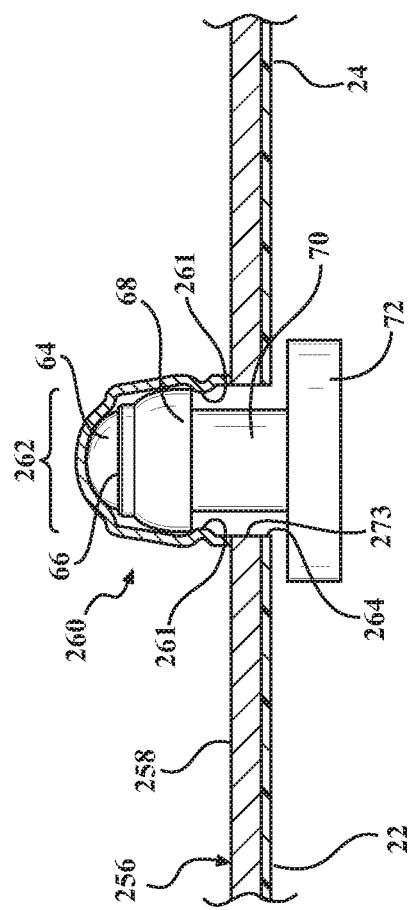
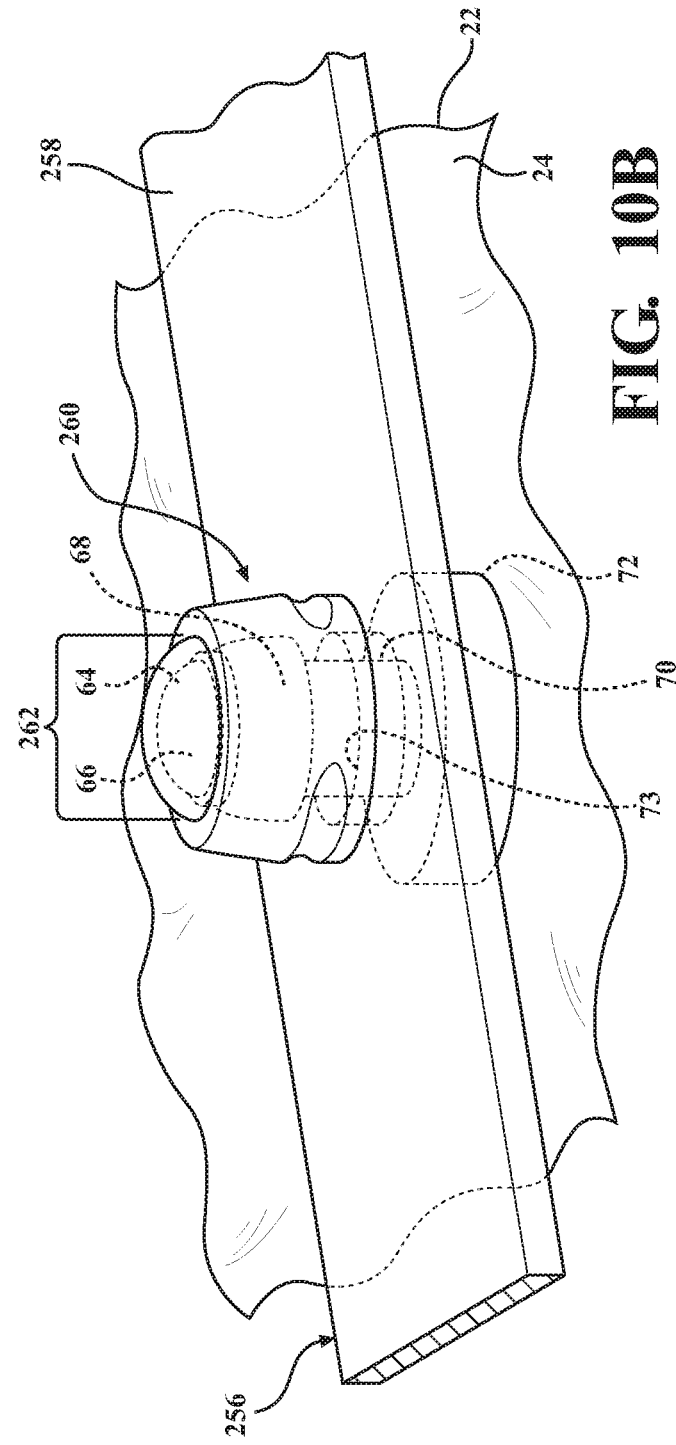

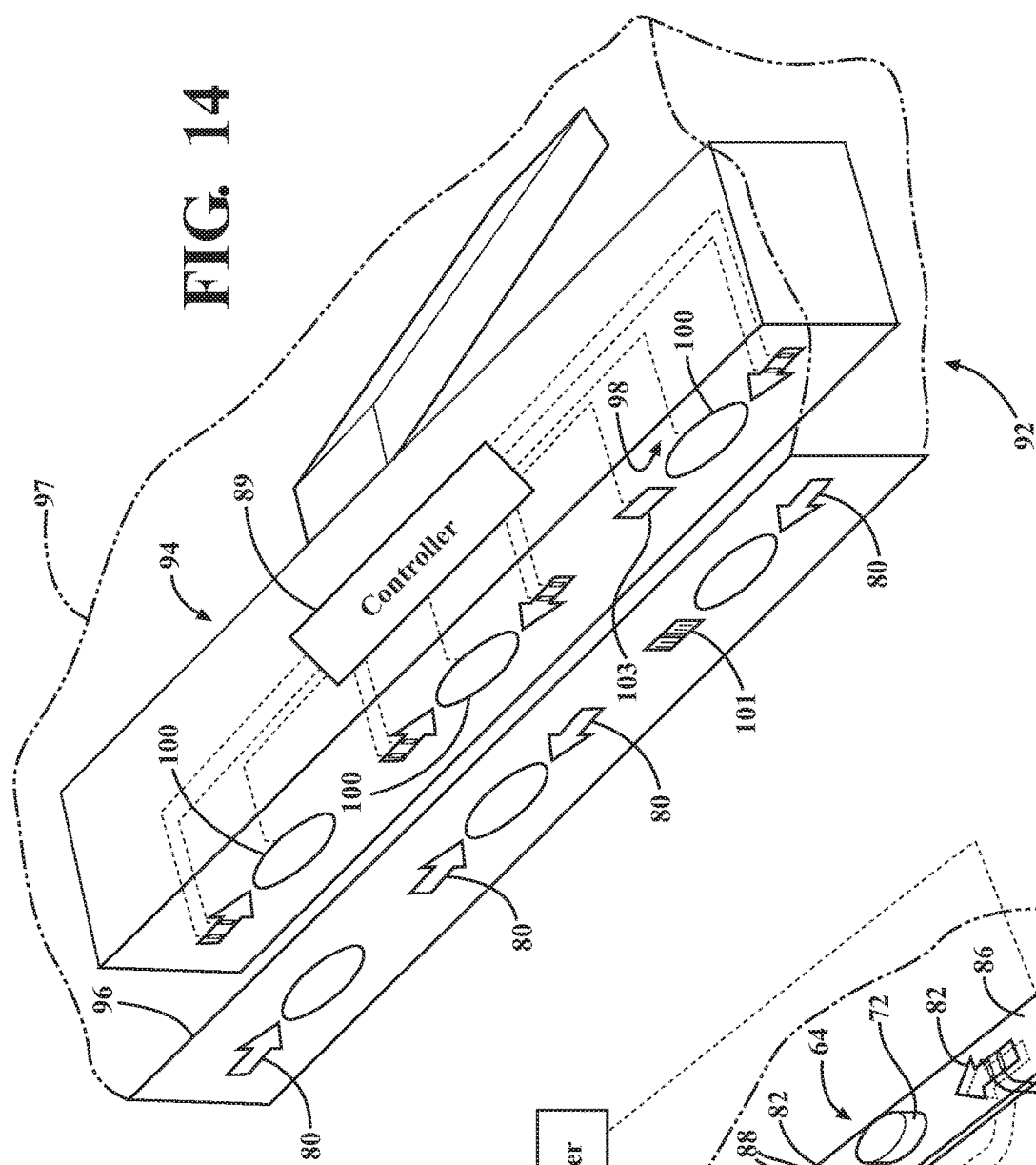
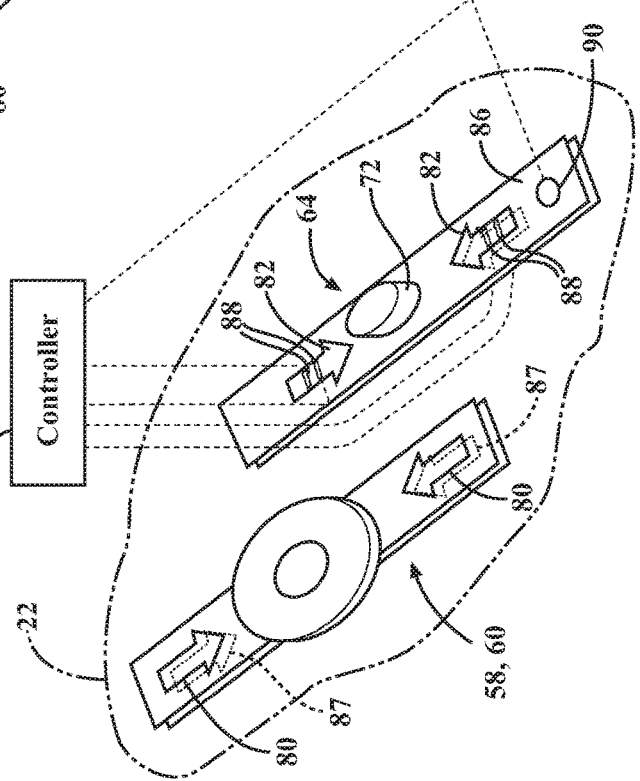

STERILE DRAPE ASSEMBLY FOR SURGICAL ROBOT

RELATED APPLICATION

This application claims priority to and the benefit of U.S. Provisional Patent Application No. 62/567,993, filed on Oct. 4, 2017, the entire disclosure of which is hereby incorporated herein by reference.

TECHNICAL FIELD

The present invention relates, generally, to sterile barrier assemblies for surgical components and, more specifically, to a sterile drape assembly for a surgical robot.

BACKGROUND

Sterile barrier assemblies such as surgical drapes are known for establishing barriers between surgical components during surgery. For instance, a surgical drape may be used to provide a barrier between a robotic arm of a surgical robot and an end effector attached to the robotic arm. In surgery, the robotic arm is treated as being nonsterile, while the end effector is sterile. The surgical drape creates a barrier between the robotic arm and the end effector to prevent contamination of a sterile field in which the end effector is operating.

Typically, surgical drapes placed between the robotic arm and the end effector have perforations or other openings through which different connections can be made between the robotic arm and the end effector, such as mechanical connections and/or electrical connections. Such perforations are acceptable, so long as they are covered during the surgery. If the end effector fails during the surgery and needs to be replaced, or if a different end effector is desired, and the perforations become uncovered, standard operating room sterility protocol may dictate that the surgical drape requires replacement before a different end effector can be installed. Removal of the surgical drape and installation of a new surgical drape takes up valuable time, so replacement is undesirable.

Other surgical drapes are not intentionally perforated, but instead are compressed between the robotic arm and the end effector. When compressed, if the surgical drape is formed of thin plastic, unintended rips or tears may occur. In addition, the surgical robot may include a cart attached to the robotic arm. The cart may be moved during surgery. The surgical drape must cover the entire robotic arm and most of the cart. Unless secured, the surgical drape may not stay in place on the cart during movement of the robotic arm and/or cart.

Placing localization components (e.g., cameras and trackers) within the surgical field requires that the components be sterilized or draped for sterility. Unfortunately, placing a drape over sensitive optics of a camera and trackers can cause localization errors if the placement of the drape is not done properly. Therefore, it is desirable to have a positive indication to the user for proper placement of the drape. It is also desirable to minimize the cost of the drape as the drape is a disposable item.

Therefore, there is a need in the art for addressing one or more of these deficiencies.

SUMMARY

In one embodiment, a sterile drape assembly is provided for a surgical robot having a robotic arm and optical tracking elements coupled to the robotic arm. The sterile drape assembly comprises a surgical drape having an arm drape portion adapted to be disposed over the robotic arm and a drape holder cooperating with the arm drape portion of the surgical drape to cover the optical tracking elements located on the robotic arm.

In another embodiment, a sterile drape assembly is provided for a surgical robot having a robotic arm. The sterile drape assembly comprises a surgical drape having an arm drape portion adapted to be disposed over the robotic arm and a ring assembly attached to the arm drape portion and configured to engage with a sterile interface plate.

In another embodiment, a surgical robot is provided. The surgical robot comprises a robotic arm, an end effector coupled to the robotic arm, a plurality of optical tracking elements attached to the robotic arm, and a sterile interface plate to couple the end effector to the robotic arm. A sterile drape assembly is also provided that includes a surgical drape having an arm drape portion disposed over the robotic arm and a drape holder cooperating with the arm drape portion to cover the plurality of optical tracking elements. The sterile drape assembly further comprises a ring assembly coupled to the arm drape portion to engage with the sterile interface plate.

BRIEF DESCRIPTION OF THE DRAWINGS

Advantages of the present disclosure will be readily appreciated as the same becomes better understood by reference to the following detailed description when considered in connection with the accompanying drawings.

FIG. 9 is a fragmentary view of one embodiment of a portion of the belt assembly of FIG. 6 illustrated with the surgical drape.

FIG. 9A is a fragmentary view of another embodiment of the portion of the belt assembly of FIG. 9 illustrated with the surgical drape.

FIG. 9B is a fragmentary view of an alternative drape holder illustrated with the surgical drape.

FIG. 10 is a perspective view of the portion of the belt assembly of FIG. 6 illustrated with the surgical drape.

FIG. 10A is a perspective view of the portion of the belt assembly of FIG. 9A illustrated with the surgical drape.

FIG. 10B is a perspective view of the alternative drape holder of FIG. 9B illustrated with the surgical drape.

FIG. 13 is a perspective view of an indicator system for indicating when the surgical drape is properly installed.

FIG. 14 is a perspective view of the indicator system for indicating when an alternative surgical drape is properly installed on a localizer camera.

DETAILED DESCRIPTION

Figure 1:
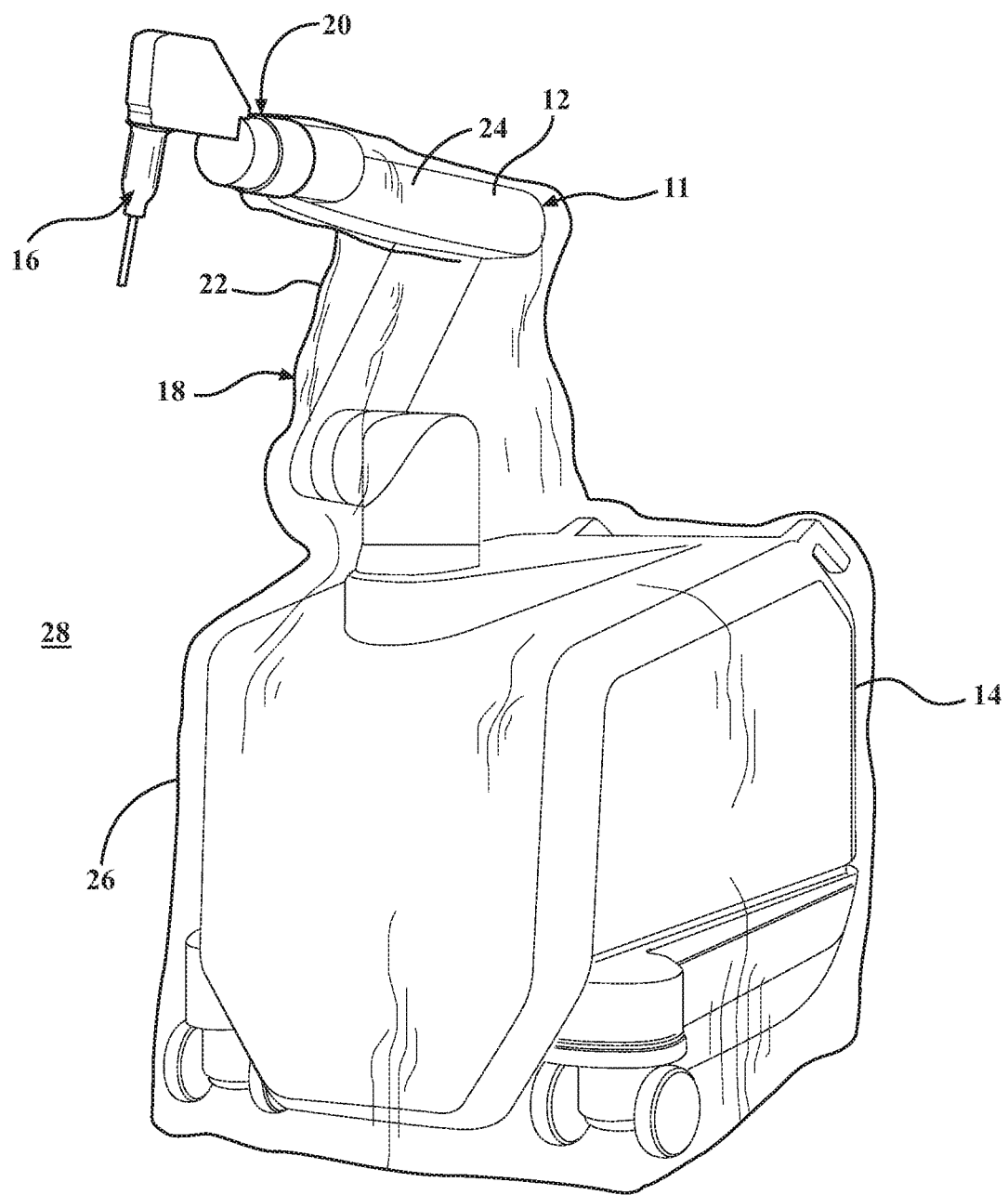
FIG. 1 is a perspective view of a robotic surgical system including a sterile drape assembly, according to one embodiment of the present invention, disposed between a surgical robot and an end effector of the robotic surgical system.

Referring now to FIG. 1, a robotic surgical system 10 is shown. In the representative embodiment described herein, the robotic surgical system 10 includes a surgical robot, generally indicated at 11. The surgical robot 11 includes a robotic arm 12 and a movable cart 14 coupled to the robotic arm 12. The robotic surgical system 10 also includes an end effector 16 coupled to one end of the robotic arm 12 of the surgical robot 11. The robotic surgical system 10 further includes a sterile drape assembly, according to one embodiment of the present invention and generally indicated at 18, used to provide a sterile barrier between the surgical robot 11 and a patient and between the surgical robot 11 and the end effector 16 coupled to the robotic arm 12, the end effector 16 being typically sterilized between uses.

The robotic surgical system 10 comprises a mounting system, generally indicated at 20, for kinematically coupling the end effector 16 to the robotic arm 12. It should be appreciated that the robotic surgical system 10 may be of a type disclosed in U.S. Patent Application Publication No. 2017/0000572 to Moctezuma de la Barrera et al., entitled "Robotic Systems and Method for Controlling a Tool Removing Material from a Workpiece", the entire disclosure of which is incorporated by reference.

As illustrated in FIG. 1, the sterile drape assembly 18 includes a surgical drape 22 to cover the surgical robot 11. The surgical drape 22 has a first or arm drape portion 24 to cover the robotic arm 12 and a second or cart drape portion 26 to cover the cart 14. The arm drape portion 24 is generally tubular in shape. The cart drape portion 26 has generally rectangular sides, but may be any suitable shape. The surgical drape 22 is made of a flexible and flaccid material such as a plastic sheet (e.g., polyurethane). In one embodiment, the arm drape portion 24 and cart drape portion 26 are separate. In another embodiment, the arm drape portion 24 and cart drape portion 26 are integral, unitary, and one-piece. It should be appreciated that the arm drape portion 24 may include radial features to allow flexing of the surgical drape 22.

The arm drape portion 24 is located over the robotic arm 12 and secured in place by the mounting system 20 to establish a barrier between the robotic arm 12 and the end effector 16 during surgery. The arm drape portion 24 extends along the robotic arm 12 and separates the robotic arm 12 from a sterile field 28 in which the end effector 16 operates. The cart drape portion 26 is located over the cart 14 and separates the cart 14 from the sterile field 28 in which the end effector 16 operates. It should be appreciated that, during surgery, the robotic arm 12 and cart 14 are considered nonsterile and the surgical drape 22 protects the robotic surgical system 10 and reduces the potential for migration of contaminants from the robotic arm 12 and cart 14 into the sterile field 28 and vice versa.

Figure 2:
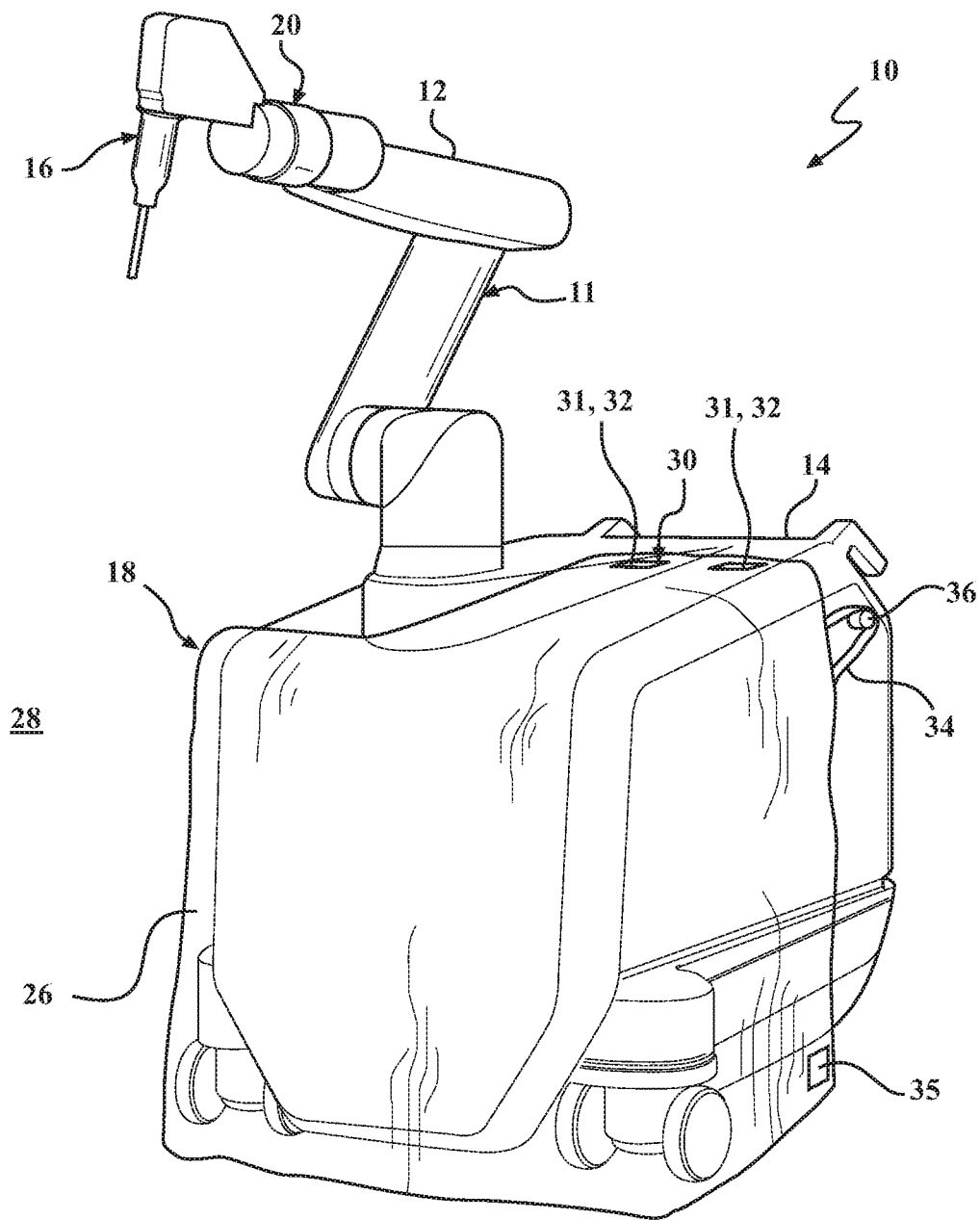
FIG. 2 is a perspective view of a portion of the sterile drape assembly of FIG. 1 attached to a cart of the surgical robot.

Referring to FIG. 2, the sterile drape assembly 18 includes a cart retaining mechanism, generally indicated at 30, to retain the cart drape portion 26 of the surgical drape 22 to the cart 14. The cart retaining mechanism 30 may include one or more metal strips 31 coupled to the cart drape portion 24 and one or more magnets 32 coupled to the cart 14 (vice versa in other embodiments, or combinations thereof). The metal strips 31/magnets 32 are coupled to the cart drape portion 26/cart 14 by a suitable mechanism such as an adhesive. The metal strips 31 and magnets 32 are spaced from each other and located at various points on the cart drape portion 26 and cart 14 to retain the cart drape portion 26 to a top and sides of the cart 14.

In another embodiment, the cart retaining mechanism 30 may additionally or alternatively include one or more straps 34. The straps 34 are coupled to the cart drape portion 26 by a suitable mechanism such as an adhesive, hook and loop fasteners (e.g., Velcro), or the like. The straps 34 form a closed loop with the cart drape portion 26. The straps 34 are located at various points on the cart drape portion 26 to secure the cart drape portion 26 to the sides of the cart 14. As illustrated, one strap 34 may be disposed over a projection or irrigation hanger 36 extending from the side of the cart 14. It should be appreciated that the straps 34 may be used in addition to the metal strips 31 and magnets 32. It should also be appreciated that the cart 14 may be made of a metal material having ferromagnetic properties to attach the magnets 32 to the cart 14. It should further be appreciated that one or more weights 35 may be coupled to the cart drape portion 26 along a bottom of the cart drape portion 26 of the surgical drape 22. A strap (not shown) may also be coupled to the cart drape portion 26 and extend across the back of the cart 14 if needed.

Referring to FIGS. 3, 4, 5A, and 5B, the mounting assembly 20 includes a sterile interface plate (SIP) or coupling, generally indicated at 38. The mounting assembly 20 also includes a first mounting portion (not shown) on the robotic arm 12 and a second mounting portion (not shown) on the end effector 16. The mounting portions may be mounting brackets, integral parts of the robotic arm 12 and/or the end effector 16, or the like. The mounting portions merely define the locations on the robotic arm 12 and the end effector 16 at which the coupling interconnects the two. The coupling 38, in combination with the sterile drape assembly 18, is configured to be located between the first and second mounting portions to provide a barrier between the first and second mounting portions (e.g., between the end effector 16 and the robotic arm 12). The coupling 38 is configured to releasably couple the first mounting portion of the robotic arm 12 to the second mounting portion of the end effector 16.

The coupling 38 includes a plate or base 40 and a plurality of kinematic couplers 42 retained by the base 40. In one embodiment, the base 40 is generally circular in shape and is formed of metal. The kinematic couplers 42 comprise three spherical balls configured to constrain six degrees of freedom of movement between the first and second mounting portions (i.e., between the end effector 16 and the robotic arm 12). In one embodiment, the balls have polished, corrosion-resistant surfaces, so that under certain loads submicron repeatability in positioning the first and second mounting portions can be achieved. The balls may be formed of ceramic, stainless steel, or other suitable materials. By way of non-limiting example, the balls may be formed of silicon carbide or tungsten carbide. It should be appreciated that the balls may be precision machined to very tight tolerances, for example less than fifty millionths of an inch.

The kinematic couplers 42 are configured to engage the first and second mounting portions and are arranged to provide a kinematic coupling between the first and second mounting portions to constrain the six degrees of freedom of movement between the end effector 16 and the robotic arm 12. An example of such a mounting assembly using kinematic couplers 42 is disclosed in U.S. Patent Application Publication No. 2016/0242861 to Flatt et al., entitled "Sterile Barrier Assembly, Mounting System, and Method for Coupling Surgical Components", published Aug. 25, 2016, the entire disclosure of which is hereby incorporated by reference.

In the embodiment shown, the sterile drape assembly 18 includes a ring assembly, generally indicated at 44, connected to the arm drape portion 24 and surrounded by the arm drape portion 24. The ring assembly 44 is configured to engage the coupling 38 so that when the coupling 38 is in position between the robotic arm 12 and the end effector 16, the surgical drape 22 can be easily pulled over the robotic arm 12 and the cart 14. The ring assembly 44 is generally more rigid than the flexible material of the surgical drape 22 and may be formed of plastic materials, such as polyethylene, polypropylene, polystyrene, polycarbonate, or the like. For example, the ring assembly 44 may be formed of polyethylene terephthalate glycol (PETG), polyetheretherketone (PEEK), or the like. In some versions, the ring assembly 44 may be formed of plastic, metal, combinations thereof, or the like.

The ring assembly 44 defines an opening 46. In the embodiment shown, the ring assembly 44 comprises a snap-ring 48, which may be formed of plastic. In one embodiment, the snap-ring 48 has a circular shape and an inner lip 55 that flexes radially outwardly when receiving the coupling 38. The snap-ring 48 also comprises a drape engagement portion that has a frustoconical shape. The surgical drape 22 is attached to the snap-ring 48 about its entire outer periphery at the drape engagement portion by ultrasonic welding, tape, adhesive, or the like (attached in FIG. 4, not attached in FIGS. 3, 5A-5F). The surgical drape 22 may be attached to an outer surface or inner surface of the snap-ring 48. The ring assembly 44 also includes a plurality of indicia 50 on the arm drape portion 24 of the surgical drape 22 adjacent the snap-ring 48 to facilitate alignment of the coupling 38 and snap-ring 48 when mating the two together. In one embodiment, the indicia 50 is configured as arrows. In another embodiment, the indicia 50 may be numbers such as 1, 2, and 3. It should be appreciated that the indicia 50 align the kinematic couplers 42 with the snap-ring 48 and associated surgical drape 22. It should be appreciated that the SIP 38 is rotatable relative to the robotic arm 12. It should also be appreciated that the SIP 38 is clocked to the indicia 50 on the arm drape portion 24 and the arm drape portion 24 is clocked to the robotic arm 12.

Figure 5A:
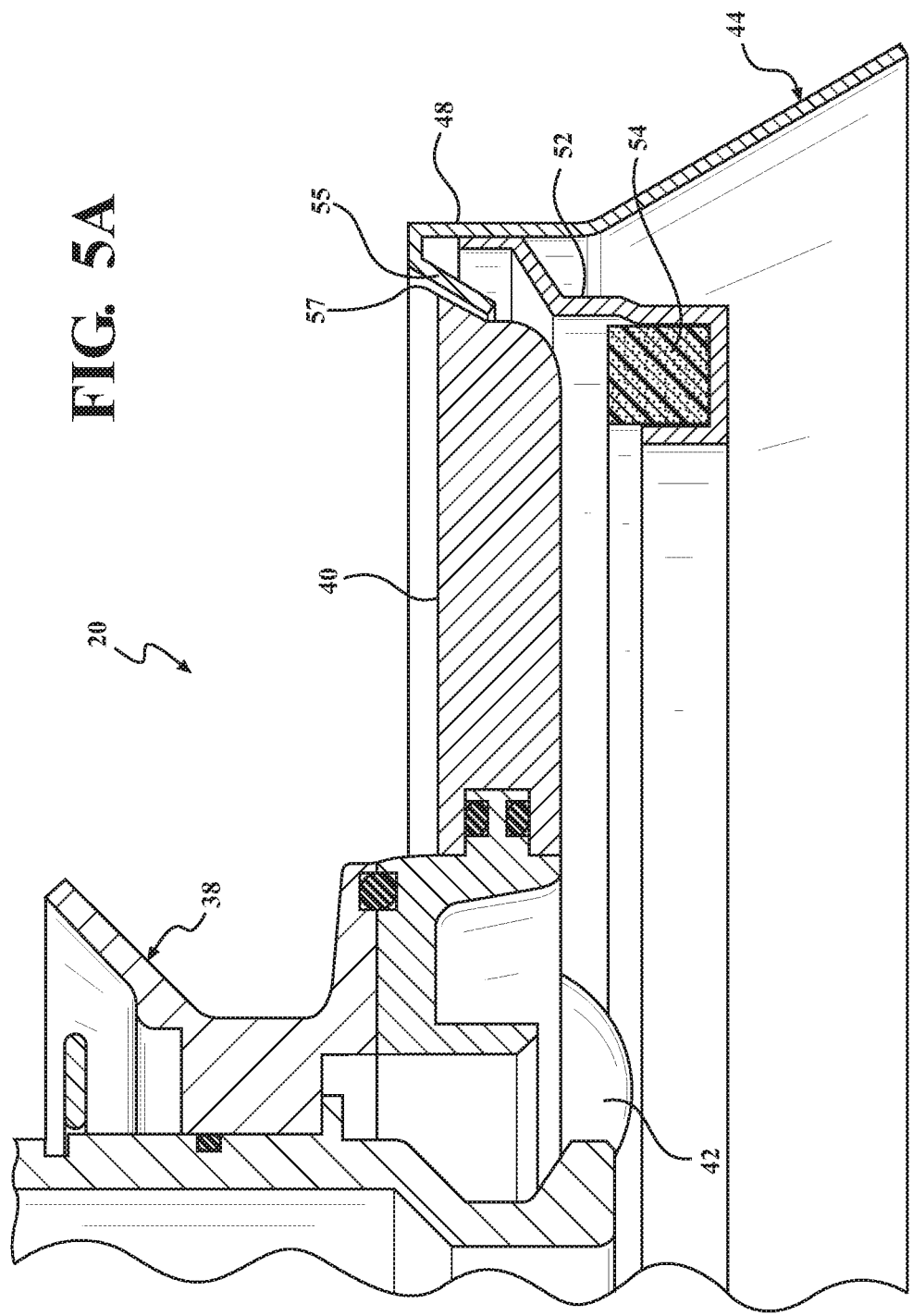
FIG. 5A is a partial fragmentary view of the mounting system of FIG. 3 illustrated in an unloaded configuration.
Figure 5B:
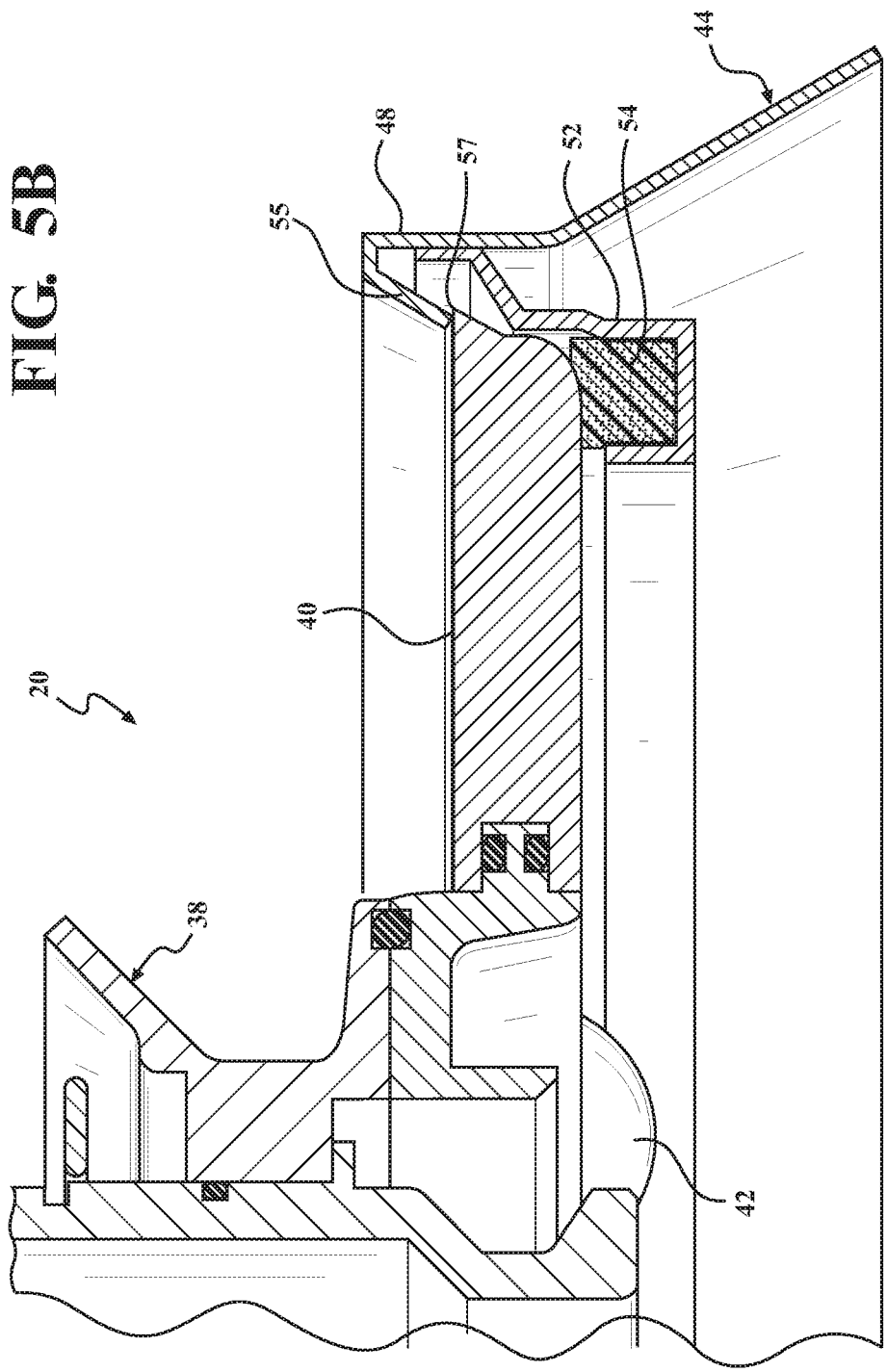
FIG. 5B is another partial fragmentary view of the mounting system of FIG. 3 illustrated in a loaded configuration.

The ring assembly 44 also includes a seal ring 52 disposed within the snap-ring 48 and a seal 54 supported by the seal ring 52 to engage and seal with the base 40 of the coupling 38 as illustrated in FIG. 5B. In one embodiment, the seal 54 is made of a foam material for a slight compression to maintain the protection barrier and allow slip rotation. It should be appreciated that the seal ring 52 may be separate or integral with the snap-ring 48.

When draping the robotic arm 12 with the arm drape portion 24 of the surgical drape 22, the coupling 38, which may be a reusable part, is first snap-fit to the snap-ring 48 of the ring assembly 44. This connection is made prior to the coupling 38 being mounted to the first mounting portion of the robotic arm 12 in the manner (or similar manner) of U.S. Patent Application Publication No. 2016/0242861 to Flatt et al., entitled "Sterile Barrier Assembly, Mounting System, and Method for Coupling Surgical Components", published Aug. 25, 2016, the entire disclosure of which is hereby incorporated by reference.

The kinematic couplers 42 are aligned with the indicia 50 on the surgical drape 22 and the coupling 38 is snap-fitted into the opening 46 in the ring assembly 44. Once the snap-ring 48 is snap-fit to the coupling 38, the coupling 38 is mounted to the first mounting portion of the robotic arm 12. It should be appreciated that the surgical drape 22 is attached to the coupling 38 so that no perforations are present or are sealed, i.e., the surgical drape 22 forms a continuous barrier with the coupling 38 through the ring assembly 44 or other similar attachment mechanism. It should also be appreciated that the seal limits contaminants from entering the sterile field 28 when the end effector 16 is removed from the sterile drape assembly 18.

Figure 3:
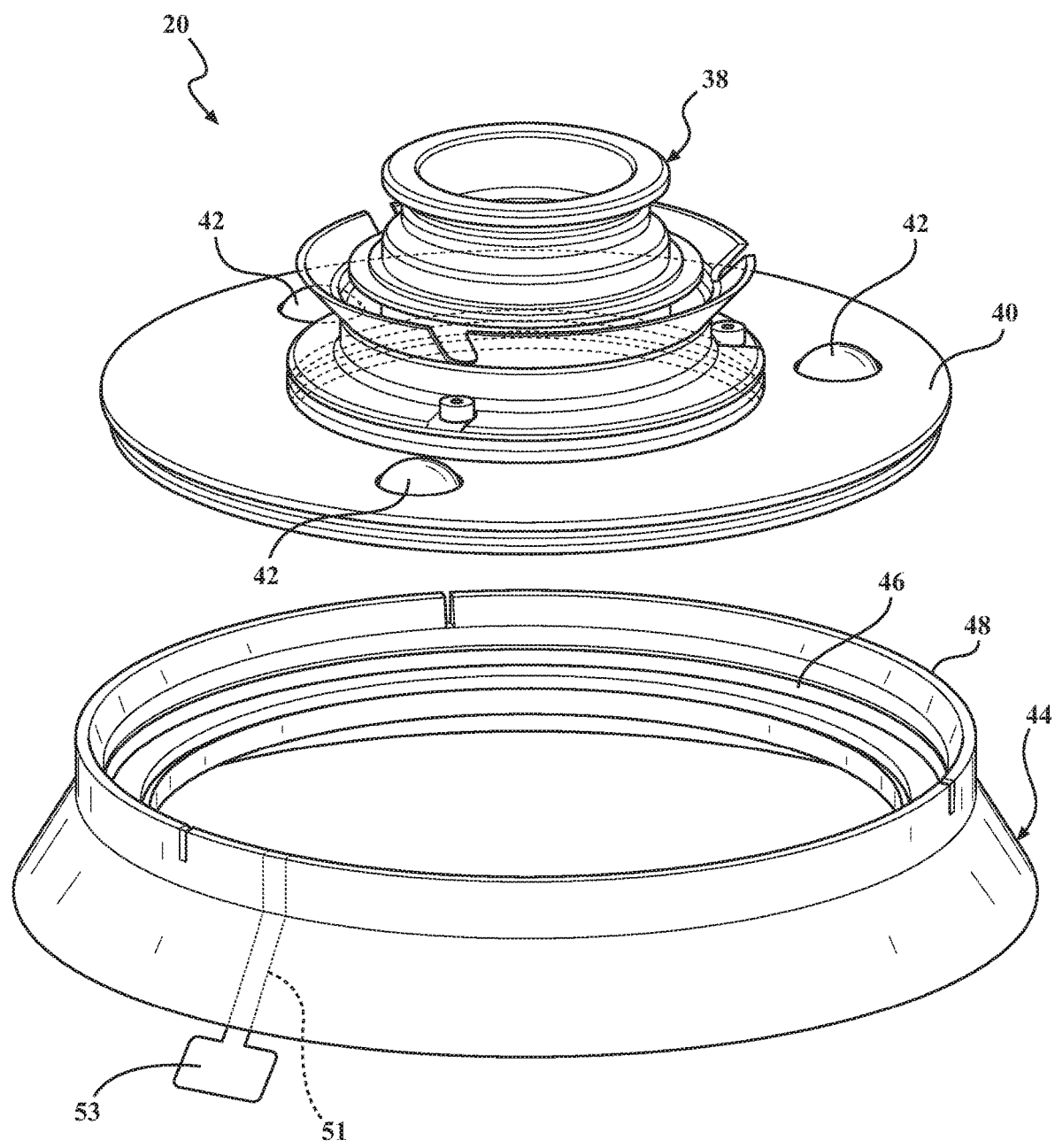
FIG. 3 is an exploded view of a mounting system for mounting a portion of the sterile drape assembly to one end of a robotic arm of the surgical robot of FIG. 1.
Figure 4:
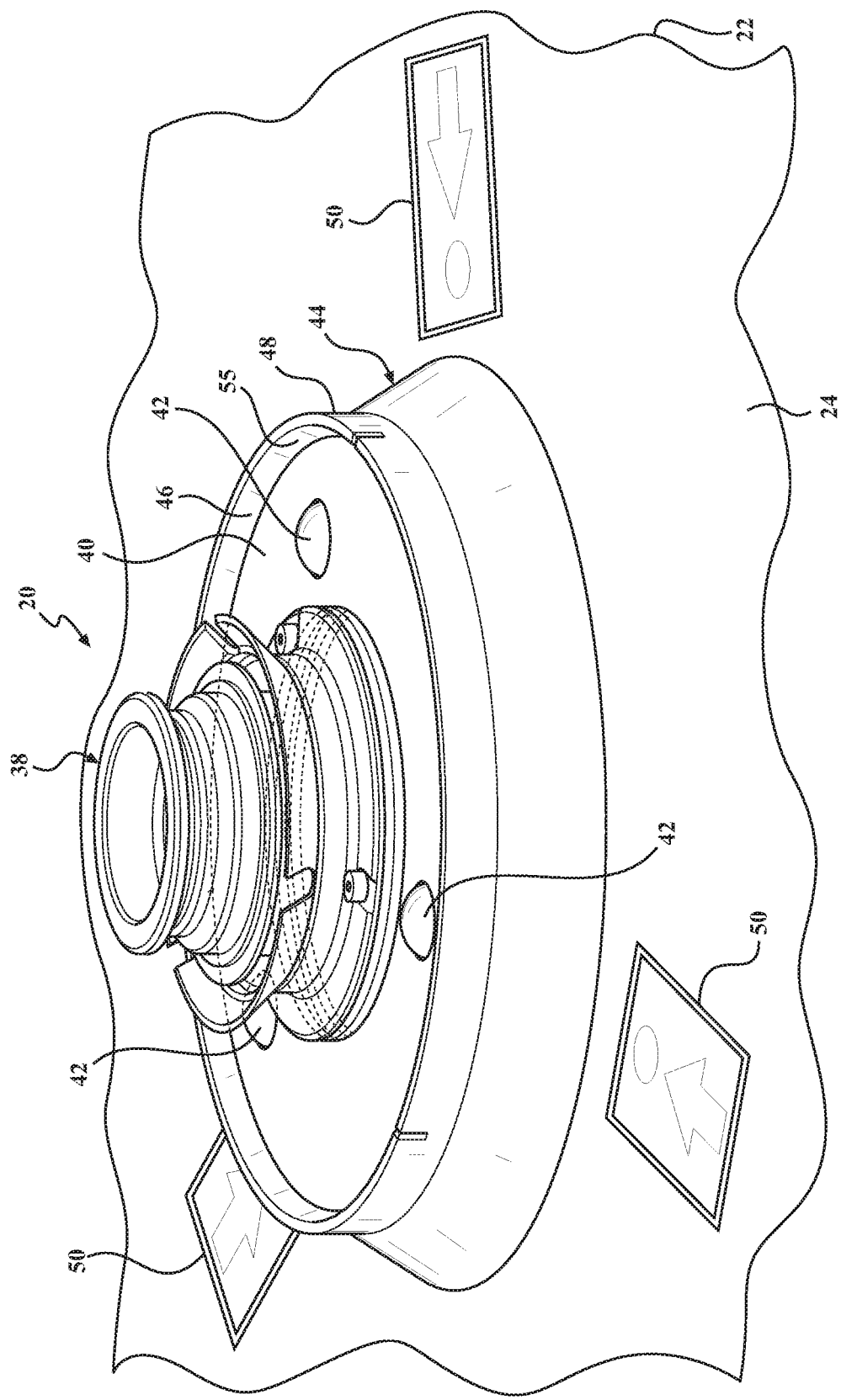
FIG. 4 is a perspective view of the mounting system of FIG. 3.

FIGS. 5A and 5B illustrate one way in which the coupling 38 is snap-fit to the ring assembly 44. As shown, the coupling 38 is pressed into the ring assembly 44 until an outer circumferential edge 57 of the base 40 protrudes past the flexible inner lip 55 (compare FIG. 5B to FIG. 5A). The outer circumferential edge 57 of the base 40 is larger in diameter than the flexible inner lip 55 of the snap-ring 48 so that when the outer circumferential edge 57 of the base 40 is pressed against the inner lip 55, the inner lip 55 flexes outwardly until the outer circumferential edge 57 passes the inner lip 55 and the inner lip 55 returns to its normal, unflexed state, as shown in FIG. 5B. As shown in FIGS. 3 and 5, the inner lip 55 may be interrupted in a plurality of locations (three shown in FIG. 3) to define a plurality of inner lip portions 55 to engage the base 40.

Figure 5C:
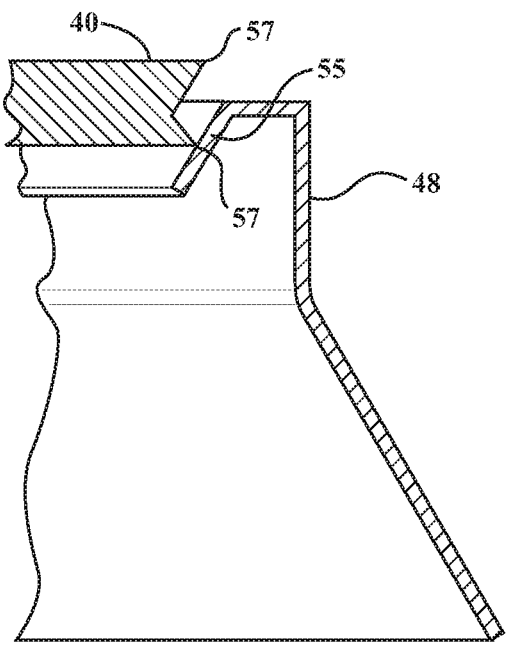
FIGS. 5C and 5D are partial fragmentary views illustrating an alternative snap-lock engagement.
Figure 5D:
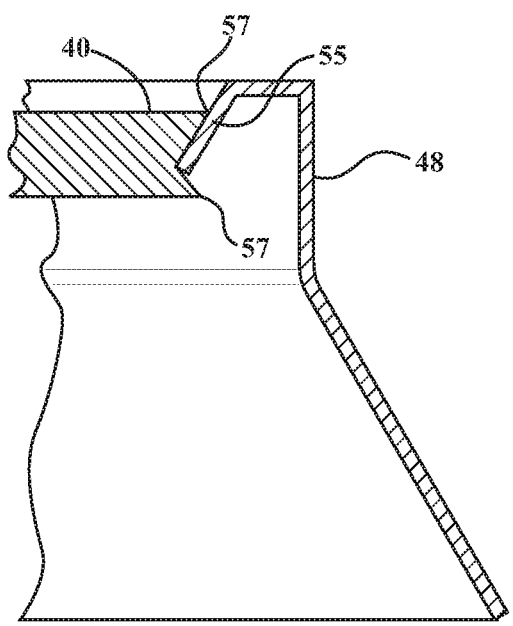
Figure 5E:
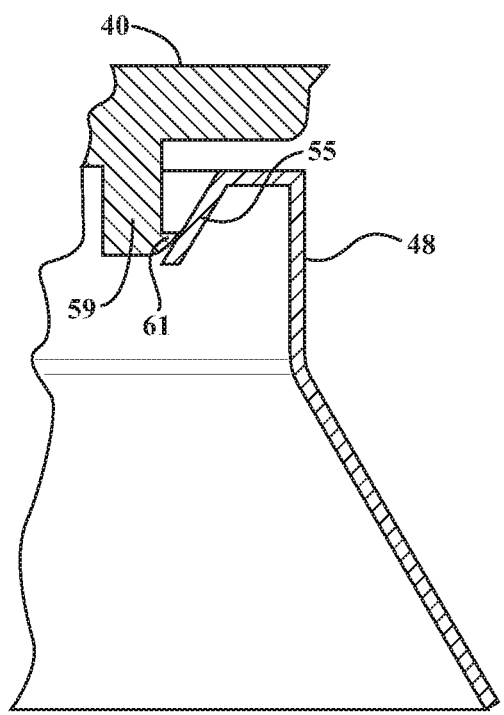
FIGS. 5E and 5F are partial fragmentary views illustrating another alternative snap-lock engagement.
Figure 5F:
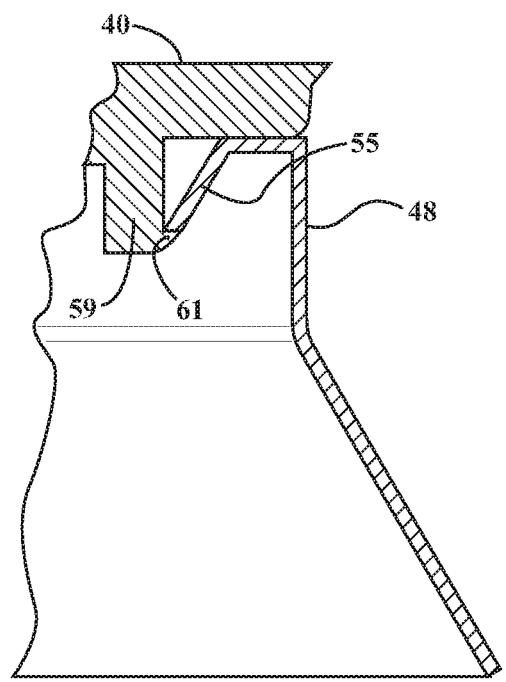
Figure 6:
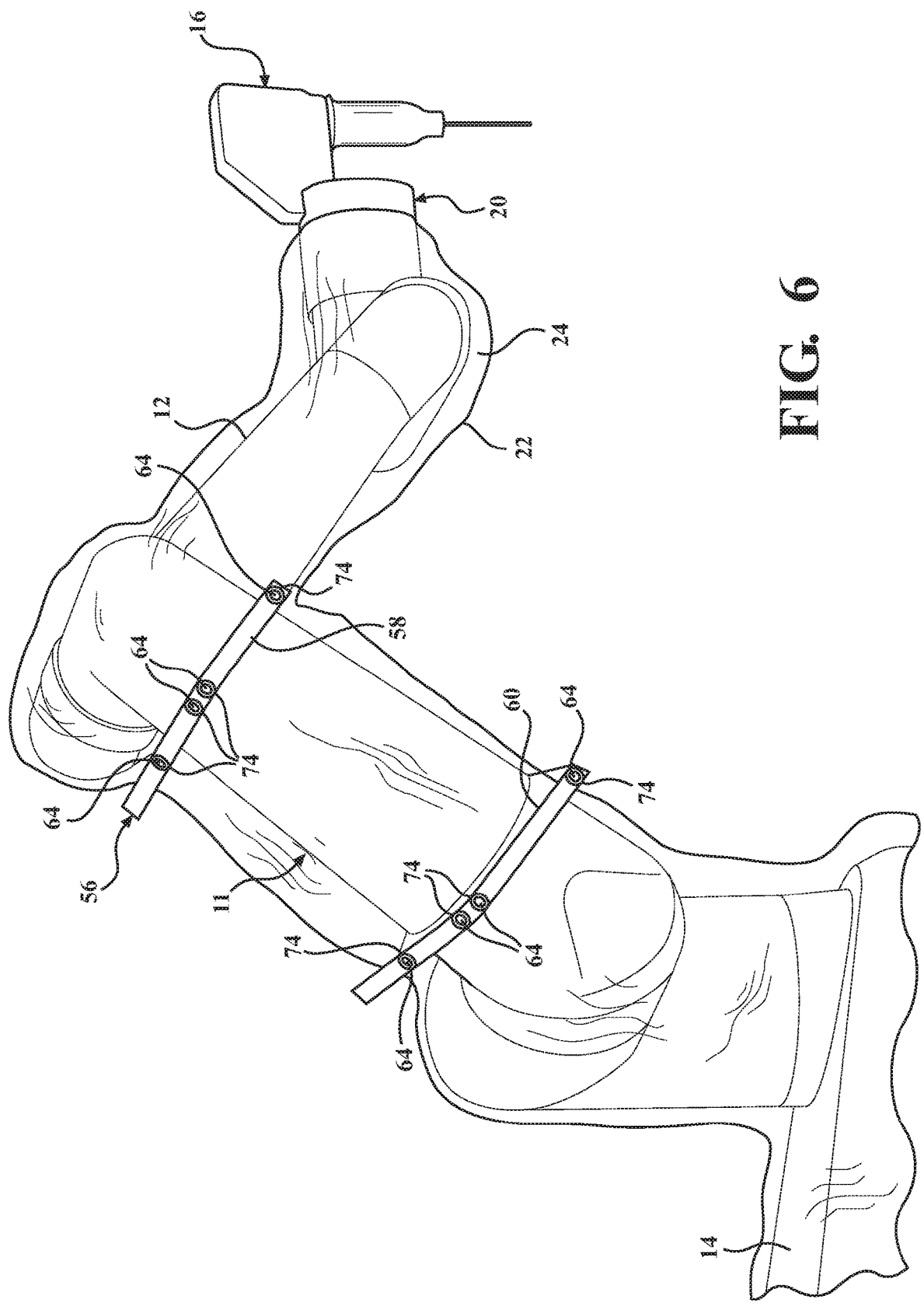
FIG. 6 is a perspective view of a belt assembly of a sterile drape assembly attached to a robotic arm.

Alternative methods of snap-fit engagement are shown in FIGS. 5C and 5D, as well as FIGS. 5E and 5F. In FIGS. 5C and 5D, the base 40 has spaced apart circumferential edges 57 that define a groove (V-shaped in one embodiment) wherein the inner lip 55 engages the groove when snap-fit together (see FIG. 5D). In FIGS. 5E and 5F, the base comprises one or more projections 59 (only one shown) with a snap-locking lip feature 61 to snap-fit to the inner lip 55 as shown in FIG. 5F. In these versions, the coupling 38 may remain rotatable relative to the snap-ring 48. It should be appreciated that the snap-ring 48 may also be referred to as a mounting ring and may attach to the coupling 38 in any suitable way, such as snap-fit, adhesive, fasteners, press fit, threads, snaps, magnets, or the like. In some cases, the ring assembly comprises only a single mounting ring, or may comprise multiple mounting rings to mount the coupling 38.

Referring briefly back to FIG. 3, ultimately the surgical drape 22 will need to be removed from the robotic arm 12 after the surgical procedure and the coupling 38 will need to be removed from the ring assembly 44. To facilitate removal of the coupling 38 from the ring assembly 44 and/or removal of the surgical drape 22 from the robotic arm 12, a tab 53 may be provided on the snap-ring 48 and connected to a perforated section 51 of the wall of the snap-ring 48. When pulling the tab 53, the perforated section of the snap-ring 38 is removed and the snap-ring 48 is split to be easily removed from the coupling 38. This could be performed while the coupling 38 remains attached to the robotic arm 12 as described above. As a result, the ring assembly 44 can be disengaged from the coupling 38, particularly in those embodiments shown in FIGS. 5C-5F in which the seal ring 52 is absent. As an alternative to the perforated section 51, the wall of the snap-ring 48 may have a thinner walled section (also represented by 51 in FIG. 3) having a much smaller material thickness than the rest of the wall of the snap-ring 48. In this case, the user can simply tear through the thinner walled section to split the snap-ring 48 and remove the snap-ring 48 from the coupling 38. Other ways of splitting the snap-ring 48 are contemplated.

Referring to FIGS. 6-12, in some embodiments, the sterile drape assembly 18 also includes a drape holder to cooperate with the arm drape portion 24 of the surgical drape 22 to cover light emitting diodes (LEDs) 64 mounted on the robotic arm 12. In one embodiment, the drape holder comprises a belt assembly 56 that includes a first drape belt 58 and a second drape belt 60. The drape belts 58, 60 are elongated when on a planar surface (see FIGS. 7 and 8). The drape belts 58, 60 are made of an elastic material, flexible plastic material, and/or combinations thereof. In one embodiment, the first drape belt 58 has a length less than the second drape belt 60. The drape belts 58, 60 may be provided separate from the surgical drape 22 and applied over the surgical drape 22 to secure the surgical drape 22 to the LEDs 64. The drape belts 58, 60 are configured to hold the surgical drape 22 on the LEDs 64 to provide a sterile barrier between the LEDs 64 and the sterile field, while also allowing adequate light to be emitted from the LEDs 64 through the surgical drape 22 for surgical navigation purposes. It should be appreciated that the drape belts 58, 60 are not required to be permanently attached to the robotic arm 12. In another embodiment, the drape belts 58, 60 may be integrated with the surgical drape 22. In yet another embodiment, the LEDs 64 may be integrated into the drape 22 and/or the belts 58, 60. The surgical drape 22 and belts 58, 60 may be separate members or integral. It should also be appreciated that the drape belts 58, 60 may be flexible or rigid.

Figure 7:
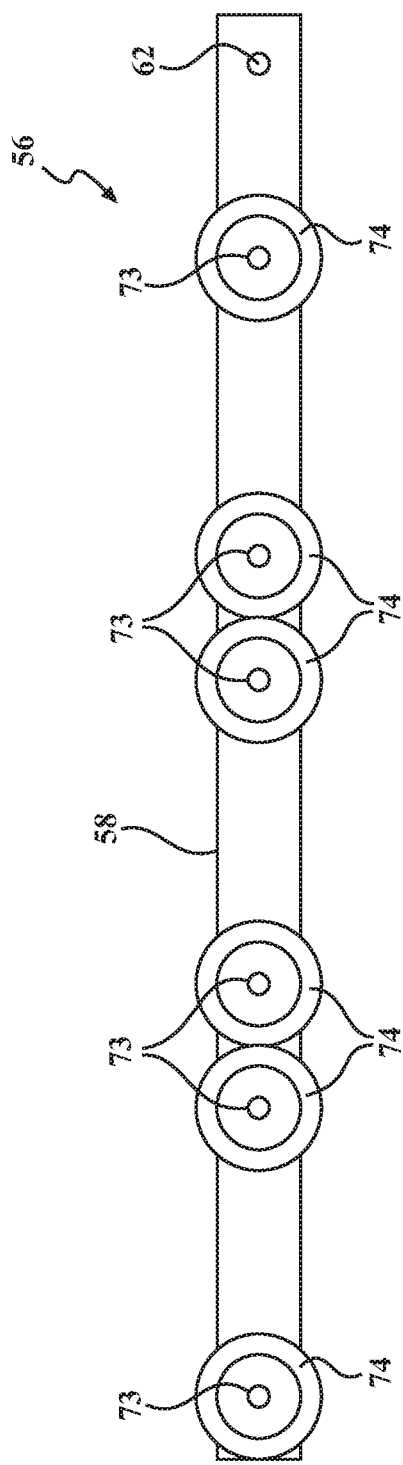
FIG. 7 is a plan view of a first drape belt of the belt assembly of FIG. 6.
Figure 8:
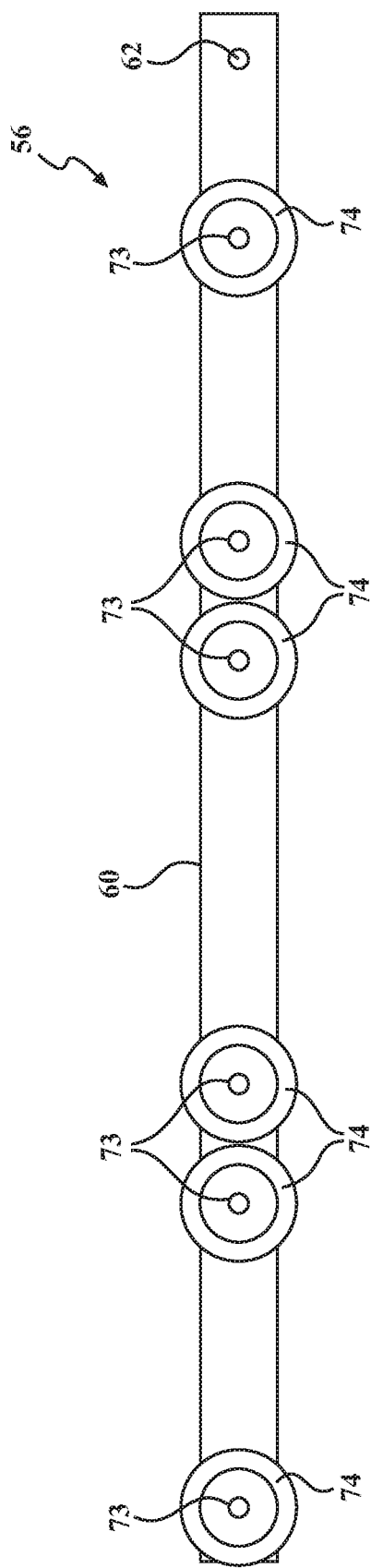
FIG. 8 is a plan view of a second drape belt of the belt assembly of FIG. 6.

Each of the drape belts 58, 60 includes a single pivot 62 at one end as illustrated in FIGS. 7 and 8. The single pivot 62 can be used to hold the drape belts 58, 60 on a pivot on the surgical drape 22 or on the robotic arm 12. The drape belts 58, 60 are thus able to pivot between left and right configurations depending on whether a left or right robotic arm configuration of the robotic arm 12 is employed.

Figure 8A:
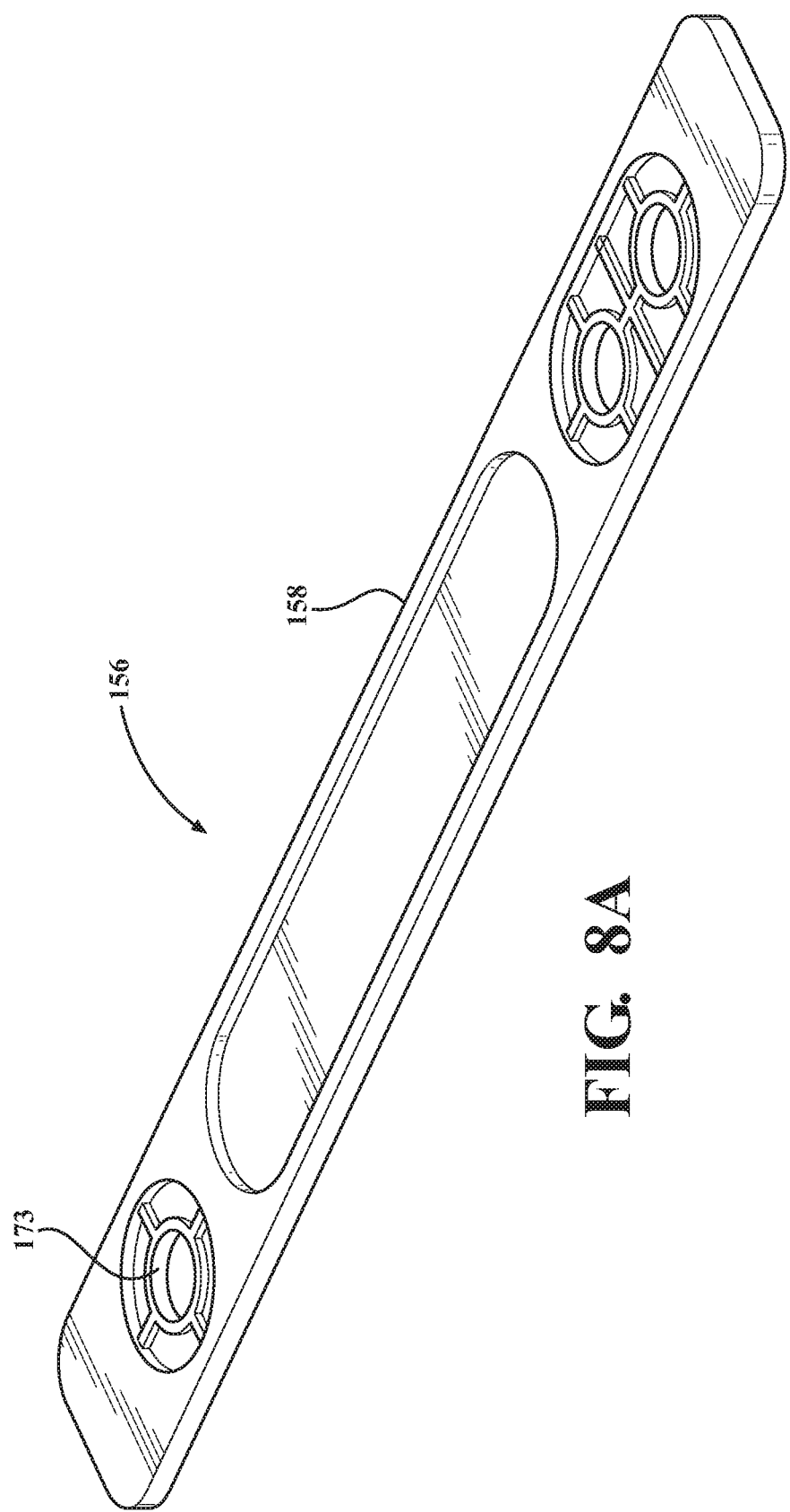
FIG. 8A is a top perspective view of an alternative drape belt.
Figure 12:
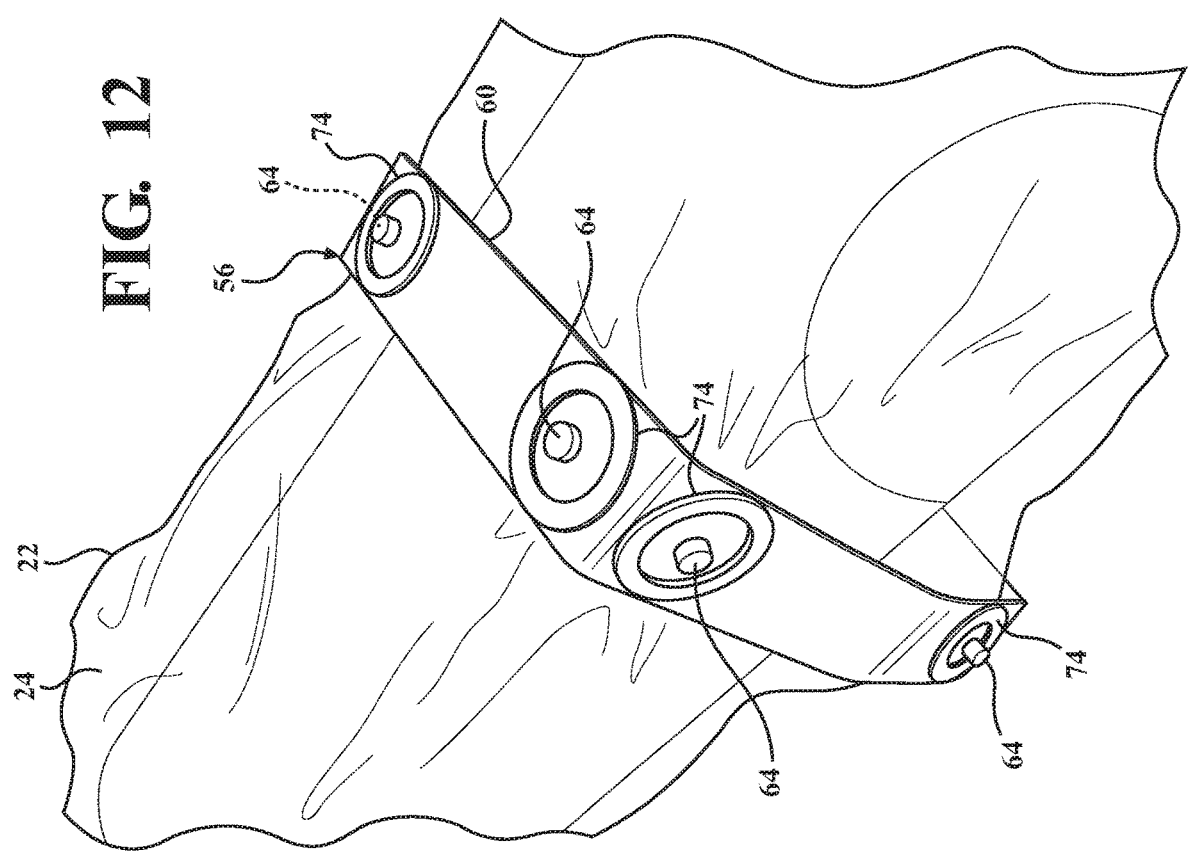
FIG. 12 is a perspective view of a second drape belt of the belt assembly of FIG. 6.
Figure 11:
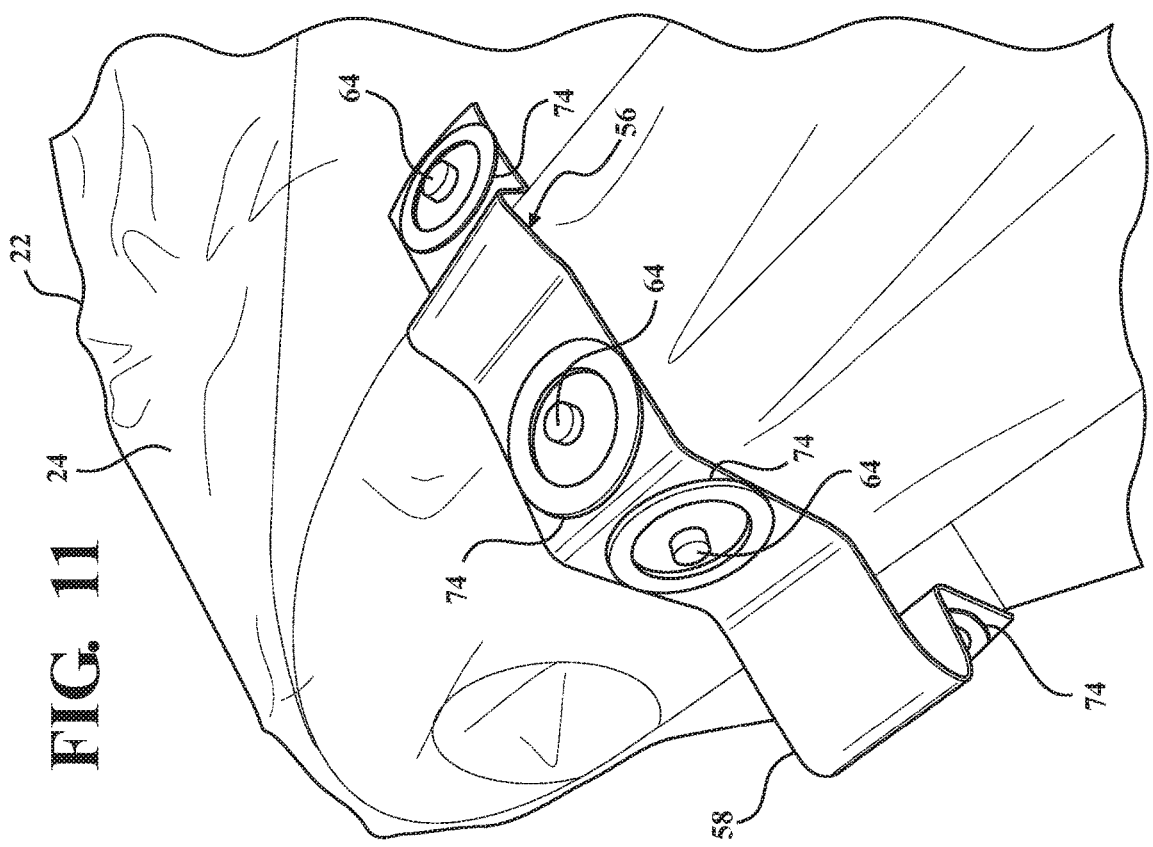
FIG. 11 is a perspective view of a first drape belt of the belt assembly of FIG. 6.

The LEDs 64 are coupled to the robotic arm 12 for purposes of surgical navigation, including tracking movement of the robotic arm 12, and by extension, for tracking movement of the end effector 16. In the embodiment shown, two sets of LEDs 64 are employed, thereby necessitating the need for at least two drape belts 58, 60. In other embodiments, only one drape belt is utilized. The drape belts 58, 60 are configured to secure the surgical drape 22 to each set of the LEDs 64 to provide a sterile barrier between the LEDs 64 and the sterile field. Other optical tracking elements, such as reflectors, optical patterns, or the like may similarly be used for surgical navigation with the surgical drape 22 secured to such optical tracking elements. In another embodiment, the LEDs 64 may be on the surgical drape 22 and a suitable securing mechanism for the LEDs 64 such as magnets (not shown) attach the LEDs 64 to the robotic arm 12. In yet another embodiment, the LEDs 64 may be attached to the drape belts 58, 60 and a suitable securing mechanism for the drape belts 58, 60 such as magnets (not shown) attach the drape belts 58, 60 to the robotic arm 12. An alternative belt assembly 156 with drape belt 158 is shown in FIG. 8A. This drape belt 158 is molded from silicone or other similar material and has apertures 173 through which the LEDs 64 are pushed to secure the drape belt 158 to the LEDs 64. In this version, the drape belt 158 would be placed over the surgical drape 22 after the surgical drape 22 is attached to the robotic arm 12 to stretch the drape material over the LEDs 64 to minimize wrinkles or air gaps.

In one embodiment, referring to FIGS. 9 and 10, each of the LEDs 64 includes a light portion 66, a support portion 68 to support the light portion 66, a capturing portion 70 extending axially from the support portion 68, and a base portion 72. The base portion 72 is adapted to attach to the robotic arm 12 directly or to attach to a navigation tracker (not shown) that attaches to the robotic arm 12. In one embodiment, the light portion 66 and the support portion 68 have outer surfaces that are generally arcuate in shape. In one embodiment, the capturing portion 70 is generally cylindrical in shape with a cylindrical outer surface. The base portion 72 is also generally cylindrical in shape, yet other shapes are contemplated.

In another embodiment, referring to FIGS. 9A and 10A, each of the LEDs 64 includes the light portion 66, the support portion 68 to support the light portion 66, the capturing portion 70 extending axially from the support portion 68, and the base portion 72. In this embodiment, the light portion 66 has outer surfaces that are generally flat or planar to maintain a flat or planar surface of the surgical drape 22. It should be appreciated that other shapes are contemplated.

The belt assembly 56 also includes a plurality of drape rings 74. In one embodiment, the drape rings 74 are generally circular in shape with flat upper and lower surfaces. The drape rings 74 are made of a rigid material such as metal and/or plastic that is relatively more rigid than the surgical drape 22. The drape rings 74 may be part of the drape belts 58, 60 or may be separate from the drape belts 58, 60 and may be affixed to the drape belts 58, 60 by adhesive or other fixation methods. It should be appreciated that the drape ring 74 may be used to secure the surgical drape 22 over a single LED 64 or a plurality of LEDs 64.

The drape rings 74 provide for tactile manipulation by the user to stretch the surgical drape 22 over the LEDs 64. For example, during use of the belt assembly 56, the surgical drape 22 is first loosely placed over each of the LEDs 64. The drape belts 58, 60 are then pushed onto the LEDs 64 via the drape rings 74, which may be affixed to the drape belts 58, 60. In some cases, one drape ring 74 is provided for each LED 64. When fitting one of the drape belts 58, 60 onto one of the LEDs 64, an aperture 73 in the drape belt 58, 60 is first located above the LED 64 (while surgical drape 22 remains between the drape belt 58, 60 and the LED 64). The drape ring 74 is then pushed toward the robotic arm 12 so that a head of the LED 64 penetrates through the aperture 73 until the drape belt 58, 60 rests about the capturing portion 70 of the LED 64 between the support portion 68 and the base portion 72.

Each capturing portion 70 has a diameter less than a diameter of the support portion 68 (and less than a diameter of the base portion 72) to further secure the drape belt 58, 60 in this location. In some cases, a diameter of the aperture 73, 173 is smaller than a diameter of the head of the LED 64 (i.e., smaller than a diameter of the support portion 68) so that the drape belt 58, 60, 158 is required to be stretched over the support portion 68 to thereby provide a tighter fit about the capturing portion 70 on the LED 64. In some embodiments, the drape belts 58, 60 have elastic membranes (not shown) attached to the drape rings 74 and extending radially inwardly from the drape rings 74 to the apertures 73 to facilitate such fitting of the drape belts 58, 60 over the LEDs

64. In the version shown in FIG. 8A, the shape of the drape belt 158 serves a similar function as the drape ring 74 by virtue of elastic portions of the drape belt 158 surrounding the apertures 173 being thinner in cross-section, and thus more flexible, while thicker portions outside this thinner region are more suitable for receiving force from the user to push the drape belt 158 onto the LEDs 64. In another version, the drape holders may simply comprise independent drape rings with elastic membranes attached to the drape rings and extending radially inwardly from the drape rings to apertures to fit over the LEDs 64. In this version, the belts 58, 60 are absent.

A space or gap may exist between the capturing portion 70 and the applicable drape belt 58, 60 when the drape belt 58, 60 is secured to the LED 64. Owing to the surgical drape 22 being located between the LEDs 64 and the belt assembly 56, when pushing the drape belts 58, 60 onto the LEDs 64, part of the arm drape portion 24 extends into each of the apertures 73 along with the head of the LED 64 and is stretched over the LEDs 64. The part of the arm drape portion 24 that stretches through the aperture 73 with the head of the LED 64 is further held in place by virtue of being trapped in the space or gap between the drape belt 58, 60 and the capturing portion 70. This dimension could be sized so that the part of the arm drape portion 24 stretched over the LED 64 remains stretched over the LED 64 during the surgical procedure. This may help to ensure that suitable light is able to be emitted from the LED 64 for surgical navigation purposes.

Referring to FIGS. 9B and 10B, in another embodiment, the drape holder comprises a belt assembly 256 that includes a drape belt 258. The drape belt 258, may be generally like the drape belts 58, 60, 158, and may be formed of an elastic material, flexible plastic material, rigid plastic material, combinations thereof, or any suitable material. In one version the drape belt 258 is transparent and formed of molded plastic, such as polyethylene terephthalate glycol (PETG), or similar material. The drape belt 258 may have apertures 273 sized so that the drape belt 258 easily fits over the LEDs 64 without any interference, or the apertures 273 may be slightly smaller than the LEDs 64 and forced over the LEDs 64 in the manner previously described. In some versions, there are two, three, four, or more drape belts 258.

The drape holder in this embodiment further comprises rigid caps 260 of transparent material, such as PETG, or similar material, attached to the drape belt 258 to mount over the LEDs 64 and snap-fit to the LEDs 64, or be secured to the LEDs 64 in some other fashion. In some cases, each of the drape belts 258 have two, three, four, or more caps 260 (e.g., spaced in the manner shown in FIGS. 7 and 8). The caps 260 are generally more rigid than the drape belt 258 and the surgical drape 22, but flexible enough to allow snap-fit engagement in the manner shown in FIG. 9B. Of course, other methods of attachment of the caps 260 are possible, such as friction fit, fasteners, or the like. As shown, the caps 260 have a top, a peripheral wall extending downwardly from the top, and an open bottom to receive the LEDs 64. The peripheral wall comprises a pair of diametrically opposed inner projections 261 that protrude radially inwardly and are normally spaced a distance slightly smaller than a diameter the support portion 68. When applying force to place the caps 260 onto the LEDs 64, the projections 261 spread apart to pass over the support portion 68, but then retract toward the capturing portion 70 as shown to secure onto the LED 64. An outer surface of the caps 260 may be partly recessed in the area of the projections 261, which may facilitate gripping of the caps 260 when attaching to or removing from the LEDs 64.

The caps 260 comprise windows 262 (e.g., transparent domes) that are suitable to allow light to pass therethrough, such as visible/near infrared light from the LEDs 64. The caps 260 may be entirely transparent such that the entire cap 260 provides the window 262 or only a portion of the cap 260 may be transparent. The caps 260 may be shaped so that the windows 262 abut the LEDs 64, such as against the light portions 66, to prevent/limit air gaps between the LEDs 64 and the windows 262.

The caps 260 are attached to the drape belt 258 about the aperture 273 via adhesive, molding, welding, fasteners, or the like. The drape belt 258 and attached caps 260 are attached to the surgical drape 22 via adhesive, molding, welding, fasteners, or the like so that the drape belt 258 and caps 260 are integral with the surgical drape 22 when fitting the arm drape portion 24 over the robotic arm 12. In this version, openings 264 may be formed in the surgical drape 22 to align with the apertures 273, as shown in FIG. 9B, so that there is no surgical drape material disposed between the window 262 and the LEDs 64. In another version, the caps 260 may be attached directly to the surgical drape 22 about the openings 264, and the drape belt 258 may be absent. In this version, the caps 260 act as the drape holder.

Once the surgical drape 22 is secured to all of the LEDs 64, i.e., by pressing the drape rings 74, pressing thicker regions of the drape belt 158, or pressing caps 260 onto each of their associated LEDs 64, the arm drape portion 24 is located between the drape belts 58, 60, 158, 258 and the robotic arm 12 and a protection barrier is maintained. The drape belts 58, 60, 158 retain the surgical drape 22 over the LEDs 64, while the drape belt 258 retains the caps 260 over the LEDs 64. It should also be appreciated that the drape belts 58, 60, 158 provide consistent LED light transmission performance through the surgical drape 22 owing to the stretching of the surgical drape 22 over the LEDs 64, while the caps 260 provide consistent LED light transmission performance by virtue of providing rigid windows 262 over the LEDs 64. It should further be appreciated that the LEDs 64 are calibrated to the robotic arm 12 and any movement of the belt assembly 56, 156, 256 may require recalibration.

Referring to FIG. 13, in another embodiment, the surgical drape 22 and/or the drape belts 58, 60 may include indicia 80 (e.g., arrows) to match up with a corresponding element 82 associated with each of the LEDs 64. In the embodiment shown, the indicia 80 is located on the drape belts 58, 60. The corresponding element 82 may be matching indicia, other indicia, or structure to which the surgical drape 22 is being mounted. The corresponding element 82 may be located on the LEDs 64 (e.g., the base portion 72), on another support 86 to which the base portion 72 is attached, or any other part associated with the LEDs 64. The other support 86 may be rigidly mounted to the robotic arm 12. The indicia 80 and corresponding element 82 guides the user to install the surgical drape 22 properly.

The user may also be notified when the surgical drape 22 is properly installed. In this embodiment, the drape belt 58, 60 includes the indicia 80 in a precise pattern that surrounds the area of the surgical drape 22 that is to be positioned over the LED 64. Additional or other forms of indicia may be employed. The indicia 80 may be associated with conductive ink or other forms of conductive elements. For example, in the embodiment shown, conductive ink 87 that is congruent with the indicia 80 is printed on an underside of the surgical drape 22. A face of the support 86 may include a plurality of corresponding conductive elements 88 that are placed to come in contact with the conductive ink 87 printed on the underside of the surgical drape 22 if, and only if (by virtue of different spacing), the surgical drape 22 is properly installed. When the surgical drape 22 is properly installed, an electrical circuit will be completed (by establishing contact between the conductive elements 88 via the conductive ink 87). A controller 89 is coupled to the conductive elements 88 to determine when the circuit is closed. In the embodiment shown, two circuits must be closed (two sets of contacts) to indicate that the surgical drape 22 has been properly installed. In other embodiments, the indicia 80 may be formed of a conductive ink printed on the drape belt 58, 60 and/or the surgical drape 22.

The controller 89 is coupled to an indicator 90 to be activated by the controller 89 to indicate to the user that proper placement of the surgical drape 22 has been achieved. The indicator 90 may comprise an indicator LED that is illuminated a first color (e.g., green/blue) for indicating proper alignment and/or the indicator LED remains illuminated a second color (e.g., red/orange) until the surgical drape 22 is properly aligned. The indicator 90 may comprise one or more of an audible indicator (e.g., speaker), visual indicator (e.g., LED), and/or a tactile indicator (e.g., a piezoelectric element). In the embodiment shown, the LED 64 itself may be coupled to the controller 89 and be illuminated by the controller 89 when the surgical drape 22 is properly placed.

In yet another embodiment, the surgical drape 22 may include a magnetic material associated with the indicia 80 that may produce an indication when the surgical drape 22 is correctly mounted to the LED 64 by being in close proximity to a corresponding sensor on the support, e.g., a hall-effect sensor. In this embodiment, the magnetic material may be printed on or embedded in the drape belt 58, 60 and/or the surgical drape 22. In some cases, the indicia 80 may be formed of the magnetic material.

Referring to FIG. 14, the indicia 80 for alignment and indication thereof could be employed on drapes for other components. For example, the indicia 80 could be applied to a surgical drape 92 for a localizer camera 94 that detects signals (e.g. IR) from the LEDs 64. In this case, the drape 92 has a flexible window 96 formed of transparent material that is connected to the flaccid material 97 of the drape 92. The indicia 80 is printed on the flexible window 96 (front or back or both). However, the indicia 80 could be printed on the flaccid material in other embodiments. The flexible window 96 is more rigid than the flaccid material and is shaped to mate to a corresponding face 98 of the camera 94 over top of sensors 100 of the camera 94. In order to enable sufficient reception of the signals from the LEDs 64, the window 96 is to be properly aligned with the face 98 in close proximity to the sensors 100. The components described above for indicating proper alignment to the user can likewise be used in this embodiment.

The surgical drape 22 may include a sensing element 101 embedded therein for the above embodiments to identify a type of the surgical drape 22 installed. The sensing element may comprise indicia such as a barcode to identify the type of the surgical drape 22 installed, RFID, or other type of identification device. The indicia may be a two-dimensional barcode printed on the surgical drape 22 that could be read by a visual sensor (e.g., barcode reader) 103 on the robotic arm 12 or the camera 94 when the surgical drape 22 is applied to the camera 94.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A sterile drape assembly for a surgical robot having a robotic arm comprising a plurality of links and a plurality of motorized joints for moving the plurality of links, a plurality of light emitting diodes located on a surface of at least one of the plurality of links of the robotic arm, the plurality of light emitting diodes projecting from the surface of the at least one of the plurality of links and each one of the plurality of light emitting diodes comprising a housing including an attachment interface, the sterile drape assembly comprising:

a surgical drape adapted to be disposed over the plurality of light emitting diodes located on the surface of the at least one of the plurality of links; and a plurality of drape attachment elements cooperating with the surgical drape and removably attachable to the surgical drape, each one of the plurality of drape attachment elements defining an aperture into which one of the plurality of light emitting diodes is inserted, each of the plurality of drape attachment elements being configured to cooperate with the attachment interface of each one of the plurality of light emitting diodes to secure a portion of the surgical drape to each one of the plurality of light emitting diodes.

2. The sterile drape assembly as set forth in claim 1, wherein each of the drape attachment elements comprises one or more rigid caps attached to the surgical drape.

3. The sterile drape assembly as set forth in claim 2, wherein each of the one or more rigid caps has a transparent window to cover one of the plurality of light emitting diodes.

4. The sterile drape assembly as set forth in claim 2, wherein each of the one or more rigid caps is configured to snap-fit to one of the plurality of light emitting diodes.

5. The sterile drape assembly as set forth in claim 1, wherein the surgical drape includes a cart drape portion adapted to be disposed over a cart.

6. The sterile drape assembly as forth in claim 5, comprising a plurality of metal strips coupled to the cart drape portion to attract magnets located at various points on the cart to retain the cart drape portion to a top and sides of the cart.

7. The sterile drape assembly as set forth in claim 1, including a ring assembly coupled to the surgical drape and configured to engage with a sterile interface plate.

8. The sterile drape assembly as set forth in claim 7, wherein the ring assembly comprises a snap-ring attached to the surgical drape and configured to engage the sterile interface plate in a snap-fit manner.

9. The sterile drape assembly as set forth in claim 7, wherein the ring assembly comprises one of a perforated section and a thin walled section for splitting the ring assembly after use.

10. The sterile drape assembly as set forth in claim 7, wherein the ring assembly includes a seal ring disposed within the snap-ring.

11. The sterile drape assembly as set forth in claim 7, wherein the ring assembly includes a seal supported by the seal ring to engage and seal with the sterile interface plate.

12. The sterile drape assembly as set forth in claim 1, wherein the attachment interface includes a support portion to support a light emitting diode, a capturing portion extending radially from the support portion, and a base portion configured to attach to the surface of the at least one of the plurality of links, each one of the plurality of drape attachment elements cooperating with the capturing portion to secure the portion of the surgical drape to each one of the plurality of light emitting diodes.

13. A surgical robot comprising:
   a robotic arm comprising a plurality of links and a plurality of motorized joints for moving the plurality of links;
   an end effector coupled to the robotic arm;
   a plurality of light emitting diodes located on a surface of at least one of the plurality of links of the robotic arm, the plurality of light emitting diodes projecting from the surface and each one of the plurality of light emitting diodes comprising a housing including an attachment interface;
   a sterile interface plate to couple the end effector to the robotic arm; and
   a sterile drape assembly including a surgical drape disposed over the robotic arm and the plurality of light emitting diodes located on the surface of at least one of the plurality of links of the robotic arm, the sterile drape assembly comprising:
      a plurality of drape attachment elements cooperating with the surgical drape, each one of the plurality of drape attachment elements defining an aperture into which one of the plurality of light emitting diodes is inserted, each of the plurality of drape attachment elements configured to cooperate with the attachment interface of each one of the plurality of light emitting diodes to secure a portion of the surgical drape to each one of the plurality of light emitting diodes; and
      a ring assembly coupled to the surgical drape to engage with the sterile interface plate.

\* \* \* \* \*